United States Patent [19]
Schuman et al.

[11] Patent Number: 6,030,212
[45] Date of Patent: *Feb. 29, 2000

[54] STACKING RESERVOIR AND SCALER SYSTEM

[75] Inventors: Robert J. Schuman, Kings Park, N.Y.; V. Richard Guilmette, Scotch Plains, N.J.; Martin I. Septimus, Forest Hills; Alfred E. Corbellini, East Northport, both of N.Y.

[73] Assignee: Dentsply Research & Development Corp., Milford, Del.

[ * ] Notice: This patent issued on a continued prosecution application filed under 37 CFR 1.53(d), and is subject to the twenty year patent term provisions of 35 U.S.C. 154(a)(2).

[21] Appl. No.: 08/723,199

[22] Filed: Sep. 27, 1996

[51] Int. Cl.[7] .................................................. A61G 17/02
[52] U.S. Cl. ................................ 433/80; 433/86; 604/259
[58] Field of Search .................................. 433/80, 82, 84, 433/86, 100; 604/259

[56] References Cited

U.S. PATENT DOCUMENTS

| | | |
|---|---|---|
| Re. 29,687 | 7/1978 | Sertich . |
| Re. 30,536 | 3/1981 | Perdreaux, Jr. . |
| D. 216,492 | 1/1970 | Johnson et al. . |
| D. 218,241 | 8/1970 | Gilbert et al. . |
| D. 369,656 | 5/1996 | Vos . |
| 2,874,470 | 5/1959 | Richards . |
| 3,075,288 | 1/1963 | Balamuth et al. . |
| 3,077,415 | 2/1963 | Ayres . |
| 3,091,033 | 5/1963 | Ellman . |
| 3,213,537 | 10/1965 | Balamuth et al. . |
| 3,368,280 | 2/1968 | Friedman et al. . |
| 3,375,583 | 4/1968 | Blank et al. . |
| 3,433,226 | 3/1969 | Boyd . |
| 3,488,851 | 1/1970 | Haydu . |
| 3,518,766 | 7/1970 | Burt . |
| 3,526,036 | 9/1970 | Goof . |
| 3,589,012 | 6/1971 | Richman . |
| 3,593,423 | 7/1971 | Jones et al. . |

(List continued on next page.)

FOREIGN PATENT DOCUMENTS

| | | | |
|---|---|---|---|
| 97288 | 1/1984 | European Pat. Off. .................. | 433/82 |
| 3934928 | 4/1991 | Germany .................................. | 433/86 |
| 87/04613 | 8/1987 | WIPO . | |

OTHER PUBLICATIONS

Dentsply/Cavitron CAVI–MED 200 Instruction Manual © 1988.
Dentsply CAVI–MED/ProSol; Periodontal Prophylaxis System; Application and Procedure Guidelines no date.
Dentsply/Equipment Division; Instruction Manual; Dentsply/Cavitron MODEL 3000; Ultrasonic Unit © 1987.
Bair et al in Periodontal Case Reports, vol. 7, Nov. 1, 1985; Method for Altering the Periodontal Pocket Environment from Anaerobic to Aerobic.

*Primary Examiner*—Ralph A. Lewis
*Attorney, Agent, or Firm*—Dale R. Lovercheck; James B. Bieber

[57] ABSTRACT

A stacking system includes a reservoir housing, a base housing and a handpiece. The reservoir housing supports a readily removable container. The reservoir housing has feet and a pivotable cover, which in closed position encloses two containers which are connected by conduits to a valve. Each container has a cap with a first and a second cap connector. Each cap connector is connected to a housing connector. The handpiece is connected by conduits through the base housing to the containers. The cover is pivotable between an open position and a closed position. The cover, in closed position, prevents the cap from moving sufficiently for the cap connector to disengage from the housing connectors. The reservoir housing is supported by and positioned above the base housing. The base housing has an upper face. The upper face has grooves. The feet are positioned in the grooves.

11 Claims, 27 Drawing Sheets

U.S. PATENT DOCUMENTS

| | | |
|---|---|---|
| 3,593,425 | 7/1971 | Robinson . |
| 3,631,631 | 1/1972 | Greenstein . |
| 3,636,947 | 1/1972 | Balamuth . |
| 3,645,255 | 2/1972 | Robinson . |
| 3,693,613 | 9/1972 | Kelman . |
| 3,703,037 | 11/1972 | Robinson . |
| 3,718,973 | 3/1973 | Slater et al. . |
| 3,760,799 | 9/1973 | Crowson . |
| 3,807,048 | 4/1974 | Malmin . |
| 3,809,977 | 5/1974 | Balamuth et al. . |
| 3,858,358 | 1/1975 | Stachowiak et al. . |
| 3,863,628 | 2/1975 | Vit . |
| 3,864,472 | 2/1975 | Pensak et al. . |
| 3,882,638 | 5/1975 | Black . |
| 3,887,701 | 6/1975 | Nachtigal . |
| 3,924,335 | 12/1975 | Balamuth et al. . |
| 3,924,806 | 12/1975 | Schowiak . |
| 3,930,173 | 12/1975 | Banko . |
| 3,956,826 | 5/1976 | Preadreaux, Jr. . |
| 3,972,123 | 8/1976 | Black . |
| 3,976,222 | 8/1976 | Spagnolo . |
| 4,012,842 | 3/1977 | Vit . |
| 4,051,337 | 9/1977 | Warrin . |
| 4,116,239 | 9/1978 | Ewen . |
| 4,148,309 | 4/1979 | Reibel . |
| 4,160,821 | 7/1979 | Sipos . |
| 4,162,576 | 7/1979 | Takemoto et al. . |
| 4,184,064 | 1/1980 | Williams . |
| 4,193,196 | 3/1980 | Kuris et al. ............... 433/82 |
| 4,193,197 | 3/1980 | Kuris et al. . |
| 4,215,476 | 8/1980 | Armstrong ............... 433/80 |
| 4,247,288 | 1/1981 | Yoshii et al. . |
| 4,248,379 | 2/1981 | Hollstein et al. . |
| 4,249,901 | 2/1981 | Wieser . |
| 4,260,380 | 4/1981 | Nash ....................... 433/119 |
| 4,276,024 | 6/1981 | Warrin . |
| 4,276,880 | 7/1981 | Malmin . |
| 4,283,174 | 8/1981 | Sertich . |
| 4,283,175 | 8/1981 | Nash . |
| 4,291,017 | 9/1981 | Beierle et al. . |
| 4,295,827 | 10/1981 | Martin et al. . |
| 4,302,186 | 11/1981 | Cammack et al. . |
| 4,302,481 | 11/1981 | Ribnitz et al. . |
| 4,315,742 | 2/1982 | Nash et al. . |
| 4,330,278 | 5/1982 | Martin . |
| 4,332,558 | 6/1982 | Lustig . |
| 4,339,432 | 7/1982 | Ritchey et al. . |
| 4,370,131 | 1/1983 | Banko . |
| 4,428,748 | 1/1984 | Peyman et al. . |
| 4,453,919 | 6/1984 | Takeshita . |
| 4,472,373 | 9/1984 | Ryan . |
| 4,487,582 | 12/1984 | Warrin . |
| 4,490,114 | 12/1984 | Kleesattel et al. . |
| 4,492,574 | 1/1985 | Warrin et al. . |
| 4,505,676 | 3/1985 | Gonser . |
| 4,522,806 | 6/1985 | Mulhemann et al. . |
| 4,582,702 | 4/1986 | Grollier . |
| 4,592,728 | 6/1986 | Davis . |
| 4,601,900 | 7/1986 | Noponen et al. . |
| 4,644,937 | 2/1987 | Hommann . |
| 4,682,949 | 7/1987 | Warrin . |
| 4,731,019 | 3/1988 | Martin . |
| 4,770,632 | 9/1988 | Ryder et al. ............... 433/28 |
| 4,793,807 | 12/1988 | Friedman et al. ............... 433/80 |
| 4,820,152 | 4/1989 | Warrin et al. . |
| 4,850,868 | 7/1989 | Wright et al. ............... 433/116 |
| 5,060,825 | 10/1991 | Palmer et al. ............... 222/25 |
| 5,087,198 | 2/1992 | Castellini . |
| 5,125,837 | 6/1992 | Warrin et al. . |
| 5,186,625 | 2/1993 | Bailey ............... 433/80 |
| 5,199,604 | 4/1993 | Palmer et al. . |
| 5,344,317 | 9/1994 | Pacher et al. . |
| 5,419,703 | 5/1995 | Warrin et al. ............... 433/216 |
| 5,478,236 | 12/1995 | Annunzio . |
| 5,503,553 | 4/1996 | Hines ............... 433/80 |

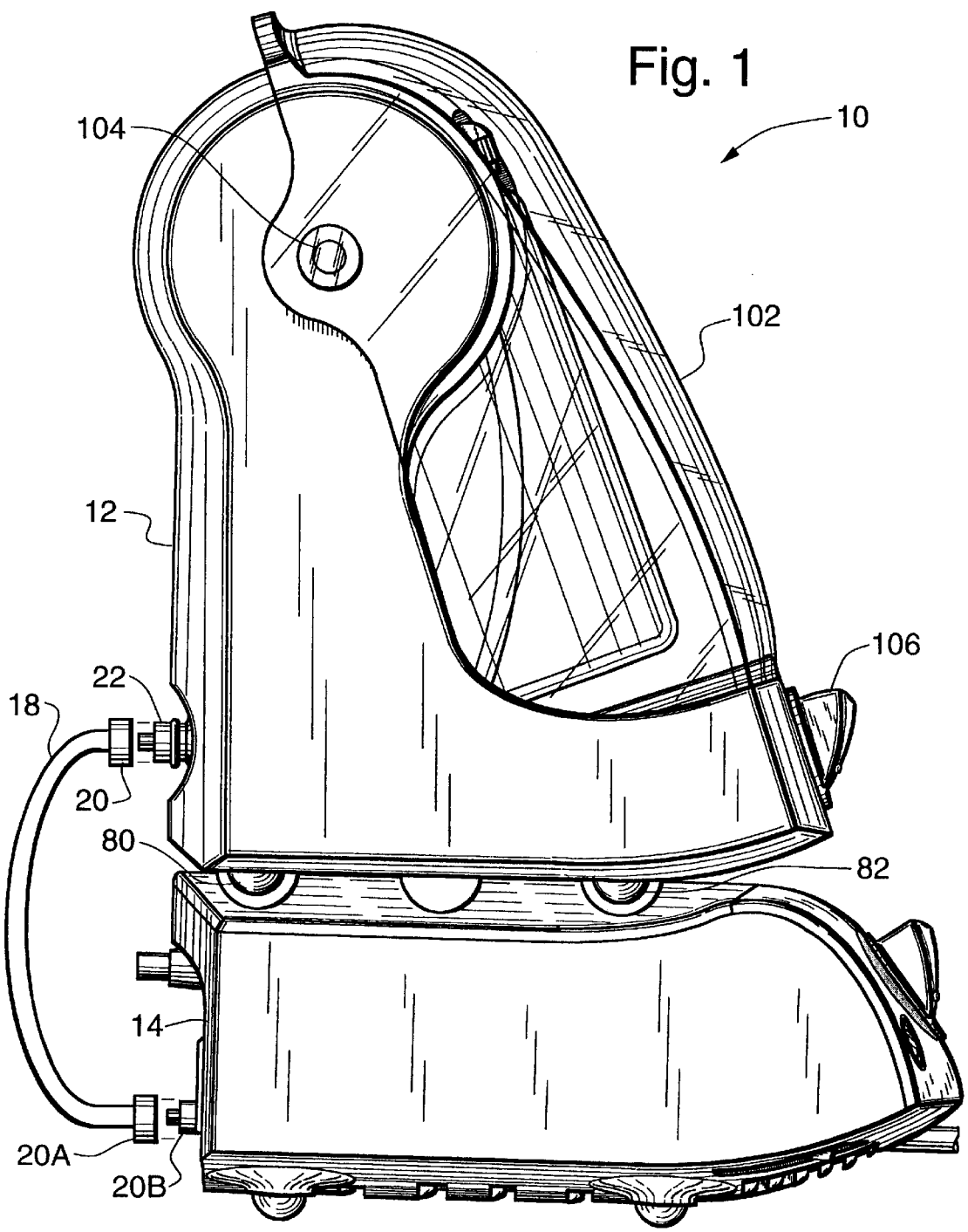

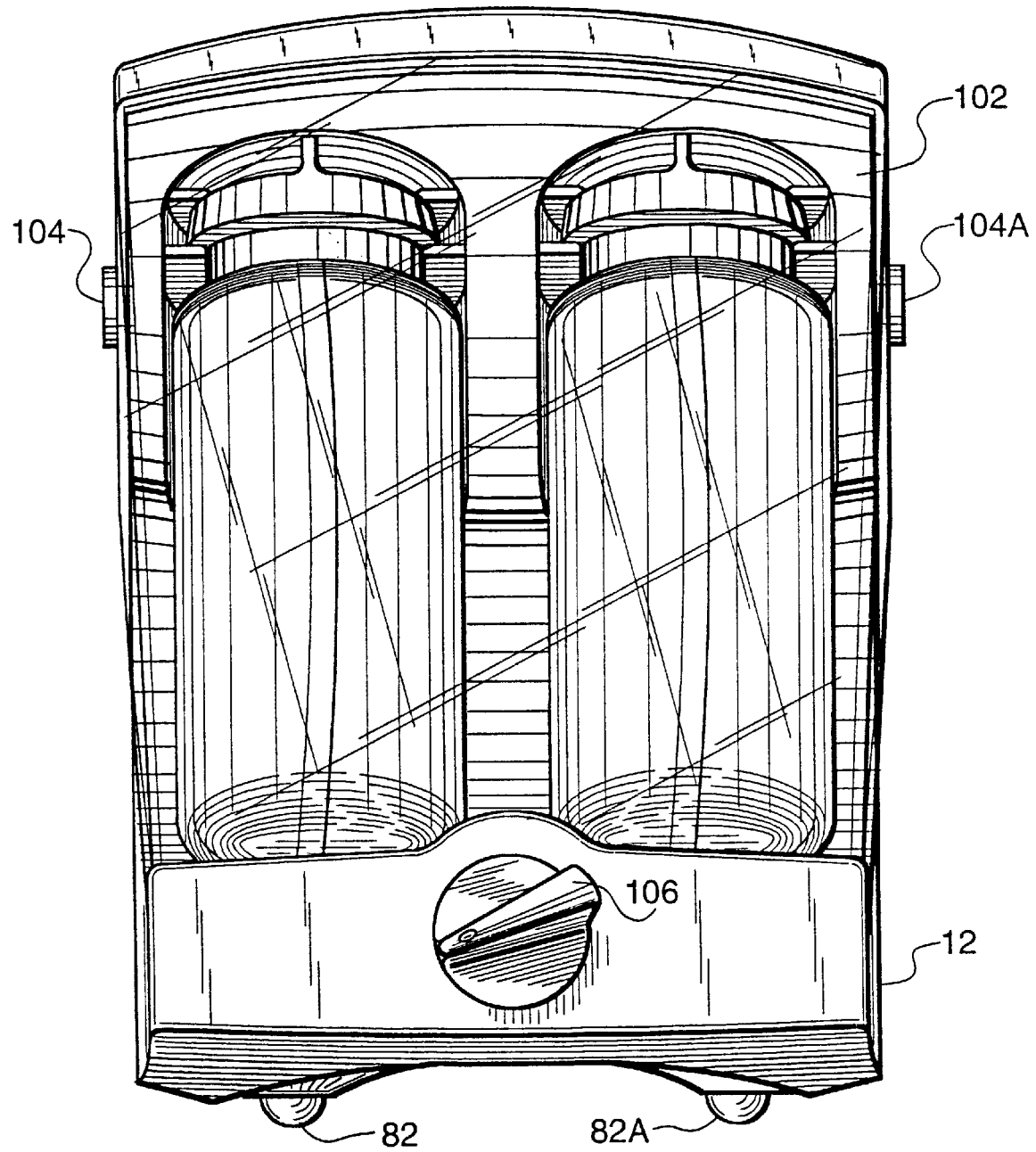

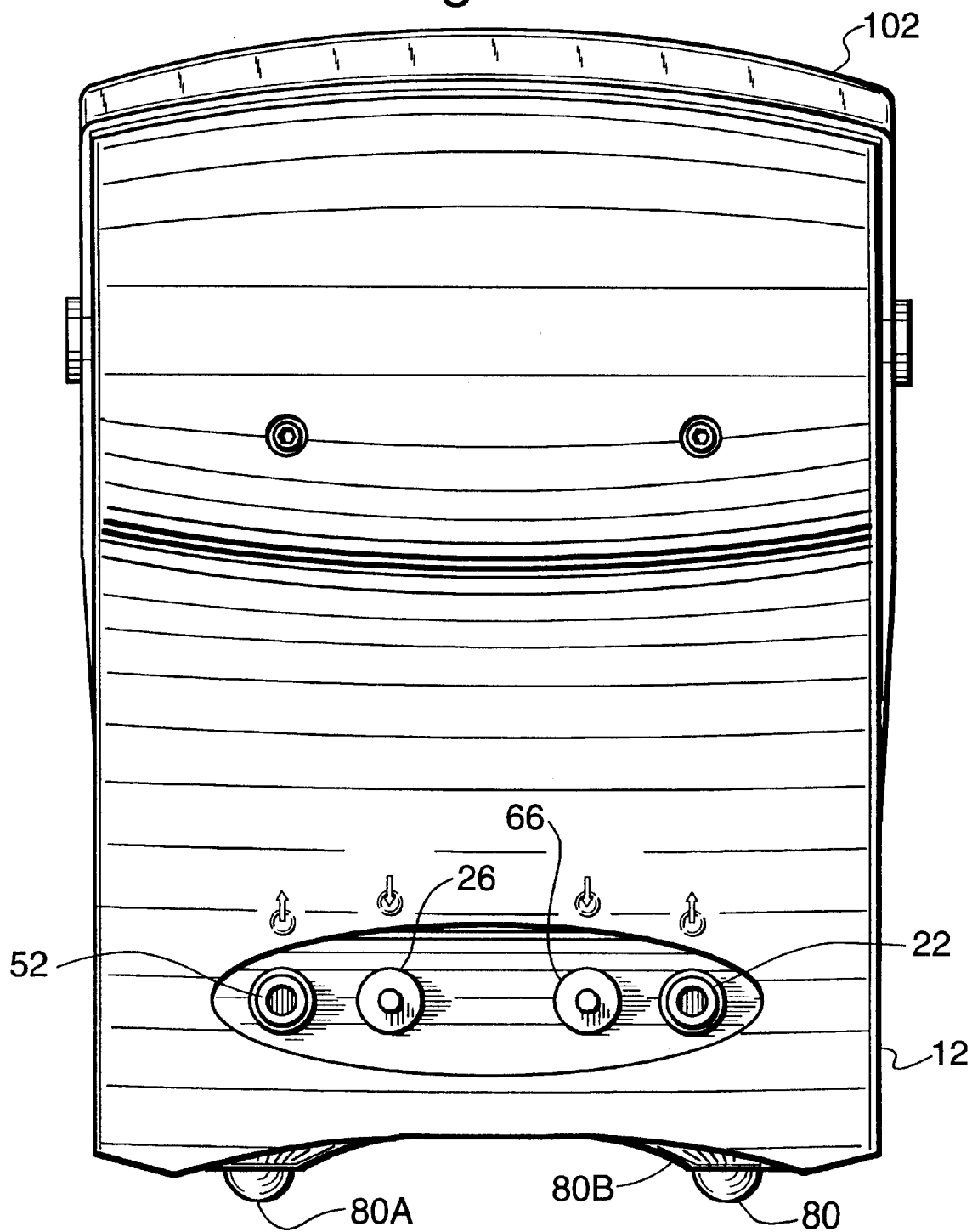

STACKING RESERVOIR AND SCALER SYSTEM

The invention relates to stacking dental scaling systems. The invention provides a stacking dental reservoir and scaling system. The present invention provides a reservoir housing having at least one container which is readily connected to a power control housing and stackable thereon. The level of liquid in each container in the reservoir housing is readily visually inspected through a clear plastic (polymeric) cover. The cover pivots on hinges to swing the lower end of the cover above the reservoir housing to open the housing for removal and/or installation of containers.

It is an object of the invention to providing a stacking ultrasonic dental tooth treatment system including an ultrasonic dental handpiece and attaching cable assembly and control housing and a fluid reservoir housing which encloses two containers, each connected to a selector valve connected to a control housing conduit connected to a handpiece conduit.

It is an object of the invention to provide a stacking fluid dispenser which includes readily removable reservoir supported by a reservoir housing having a cover which is pivotable between an open position and a closed position and an interlock valve which is closed by the cover when the cover is in its open position.

It is an object of the invention to provide a stacking dental reservoir and scaling system.

It is an object of the invention to provide a stacking dental scaler system having a reservoir housing with a clear plastic cover which pivots on hinges to swing the lower end of the cover above the reservoir housing to open the housing for the removal and/or installation of containers, as is provided by the present invention.

It is an object of the invention to provide a stackable reservoir housing having a self contained three position selector valve connected in fluid flow communication to a source of air pressure for dispensing from either of two reservoir liquid containers or from a water supply through the selector valve. In a preferred embodiment of the invention only fluid from any one of the containers is conveyed to the handpiece and the system is not connected to an external water supply. By so doing the system can dispense clean water. The system can also be connected to an external water supply, which can also be dispensed to a scaler system.

Warrin et al in U.S. Pat. No. 5,419,703 discloses a method of subgingival scaling and lavage. The apparatus disclosed in Warrin et al includes reservoirs for storing medicament inside a base unit.

The invention solves the problems of the prior art fluid dispensing dental system.

BRIEF DESCRIPTION OF THE DRAWINGS

FIG. 1 is a side view of the right side of a stackable reservoir housing stacked upon a scaler housing in accordance with the invention.

FIG. 2 is a front view of the stackable reservoir housing shown in FIGS. 1–9.

FIG. 3 is a rear view of the stackable reservoir housing shown in FIGS. 1–9.

BRIEF DESCRIPTION OF THE INVENTION

Figure 1A:
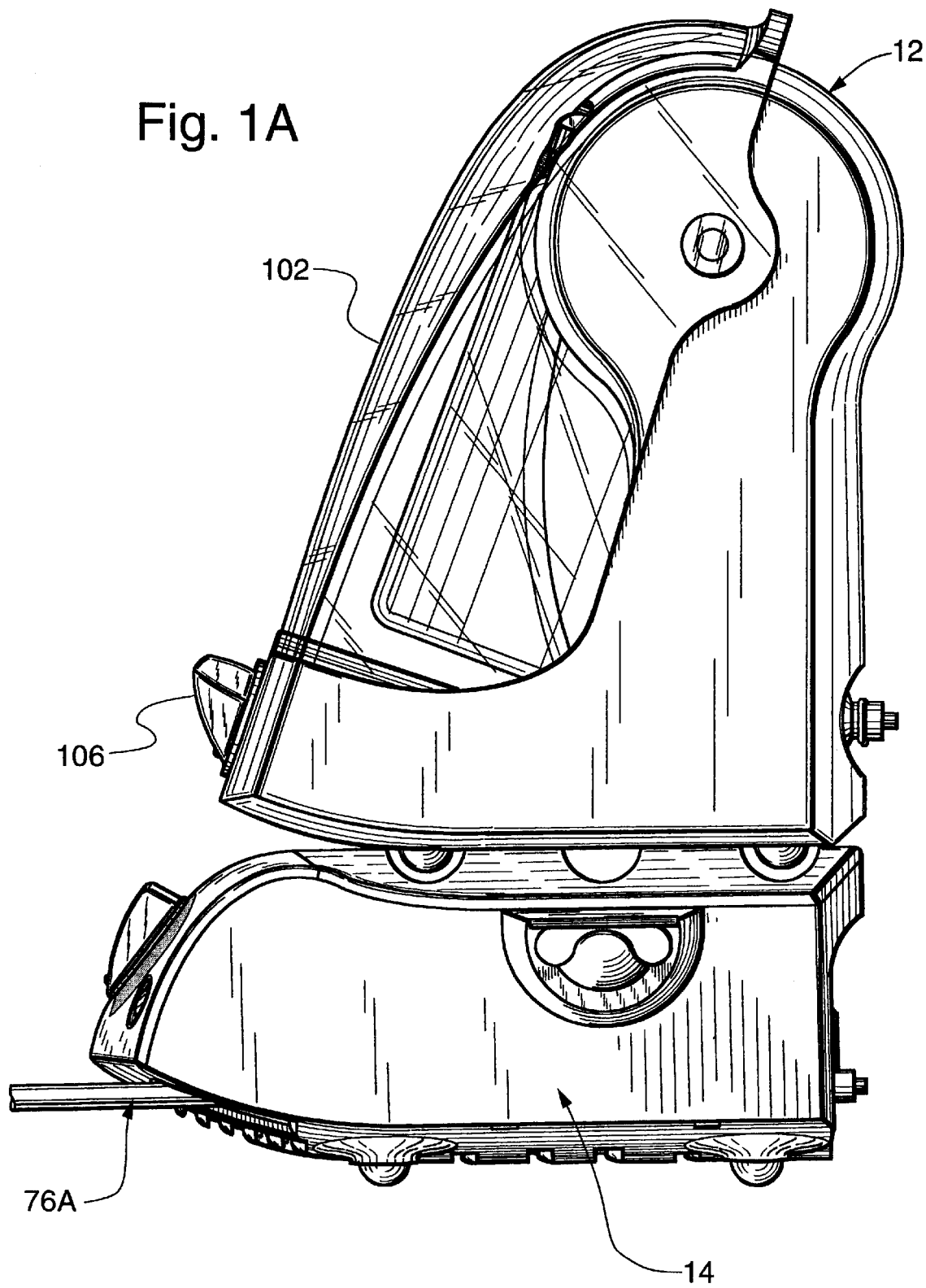
FIG. 1A is a side view of the left side of the stackable reservoir housing stacked upon a scaler housing shown in FIG. 1.

A stacking system includes a reservoir housing, a cover, a base housing and a handpiece. The reservoir housing supports two readily removable containers. The reservoir housing has feet and is pivotally connected to the cover. With the cover in closed position, the cover and reservoir housing enclose both containers. Each container has a cap with a first and a second cap fluid flow connector, which are connected to the first and second housing connectors. The first housing connector is connected to the first cap connector. The second housing connector (505) is connected to the second cap connector. The handpiece is connected by conduits through the base housing and reservoir housing to the containers. The cover is pivotable between an open position and a closed position. The cover in closed position prevents the cap from moving sufficiently for the cap connector to disengage from the housing connector. The reservoir housing is supported by and positioned above the base housing.

The base housing has an upper face. The upper face has grooves. The feet being positioned in the grooves. Each container is in fluid flow communication with the handpiece. Preferably, the container is connected to a venting valve, and the venting valve is connected to a source of air pressure at a pressure of at least 35 psi. Preferably, the reservoir housing supports a second readily removable container. Preferably, the base housing encloses a scaler conduit (392A). Preferably, the reservoir housing is connected by a conduit (18) to the scaler conduit. Preferably, the dental dispenser has a bottom wall and at least one readily removable container supported by a reservoir housing which has a pivotable cover and a venting valve (50) and the cover is adapted to be opened for removal of the container from the reservoir housing. Preferably, the container encloses a medicament containing fluid. Preferably, the container is enclosed by the reservoir housing when the cover is in closed position. Preferably, the base housing has feet.

The invention provides a stacking system comprising fluid reservoir housing, a base housing, and an ultrasonic dental handpiece having a coil. The reservoir housing has feet. The feet are supported by the base housing. The reservoir housing enclosing a first container and a second container. The first and second containers are connected in flow fluid communication through a venting valve to the handpiece. The base housing encloses a power control circuit. The power control circuit is connected to the coil in the handpiece. The reservoir housing has a cover. The reservoir housing has a reservoir fluid flow connector, which engages a container connector. The lid is positioned to prevent movement of the container whereby the container connector is held in the reservoir connector, while the lid is in closed position. Preferably, the pivotable cover is transparent. Preferably, the cover has a closed position and the cover in the closed position prevents the cap from moving sufficiently for the cap connector to disengage from the housing connector.

The invention provides a stacking system comprising a fluid reservoir housing (12), a base housing (314), and a dental handpiece (316) having a tip (316A). The reservoir housing is supported by feet. The feet are positioned on an upper face to the base housing. The reservoir housing enclosing a first container and a second container. The first and second containers are connected to a venting valve. The venting valve is connected to the first and the second container. The first and the second container are connected in fluid flow communication with the tip through a conduit in the base housing.

DETAILED DESCRIPTION OF THE INVENTION

Figure 14:
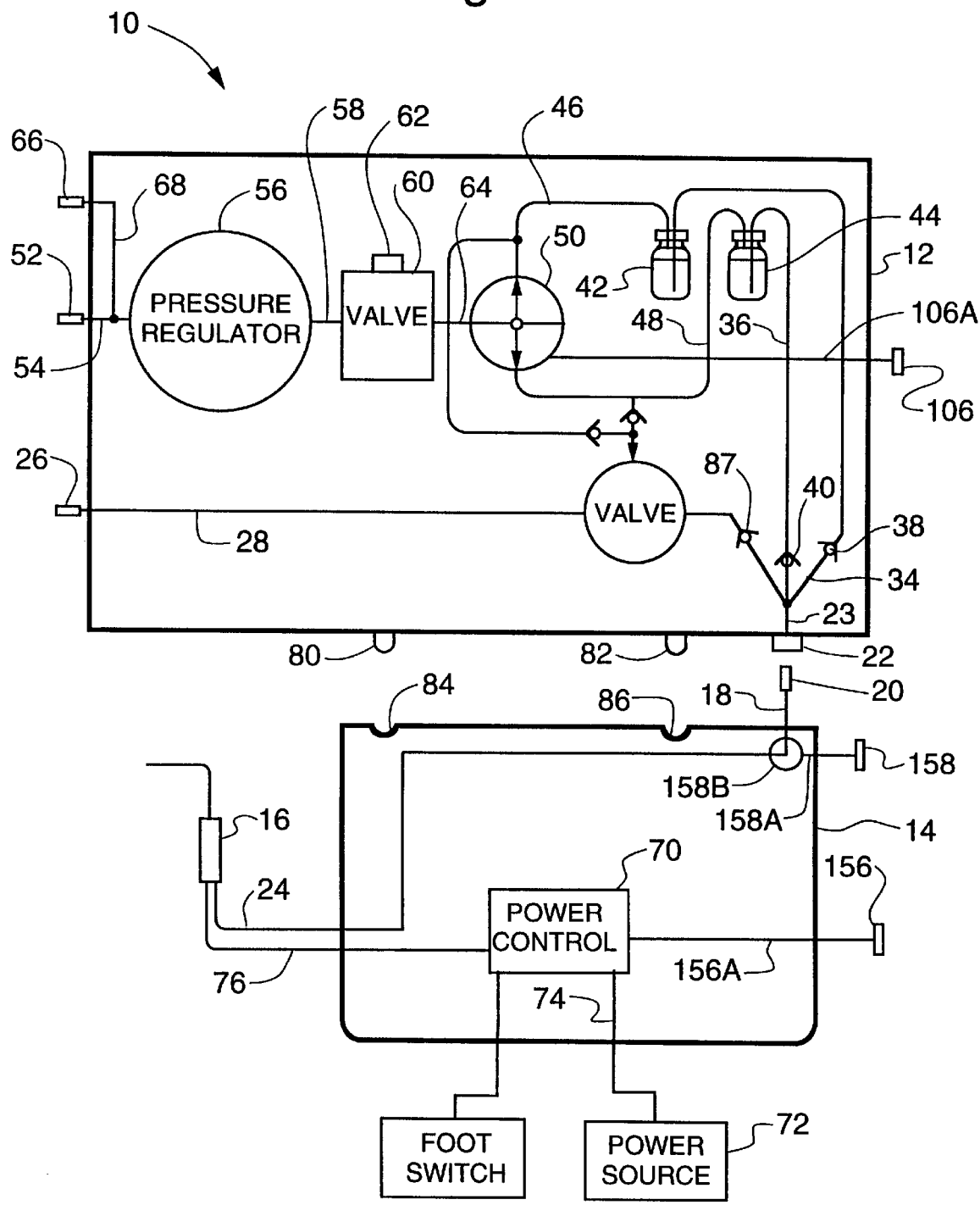
FIG. 14 is schematic diagram of the stacking dental reservoir and scaling system shown in FIGS. 1, 1A and 1B.

The invention is now described with more particular reference to FIGS. 1–19. It is seen that stacking dental reservoir and scaler system 10 includes a reservoir housing 12 and a scaler housing 14 and a handpiece 16 as shown in FIGS. 1 and 14. The scaler housing 14 is connected through fluid conveying conduit 18 to coupler 20 which has a shutoff valve. Coupler 20 is inserted in fluid type connection into coupler 22 which has a shut-off valve. Coupler 22 connects fluid conveying conduit 23 to conduit 18. Conduit 18 is connected by couplers 20A and 20B through solenoid valve and flow control device to conduit 24 to convey fluid into ultrasonic handpiece 16.

Coupler with automatic shut-off valve 26 is adapted to be connected to a water supply, which preferably has a pressure of at least 10 psig. Preferably, the water supply has a pressure of at least 20 psig. More preferably the water supply has the pressure of about 60 psig. Water is conveyed from the water supply through the coupler and shut off valve 26 through conduit 28 to air pilot valve 30. Water is conveyed from air pilot valve 30 through conduit 32 into conduit 23, and conduit 18 through a solenoid valve and flow control device into conduit 24 and into handpiece 16. Conduits 34 and 36 have check valves 38 and 40 respectively and are connected to reservoir containers 42 and 44 respectively. Containers 42 and 44 have caps 41 and 43 respectively. In use a container (42 or 44) may be filled with a medicament containing fluid. Conduit 32 has check valve 87 and is connected to air pilot valve 30.

Reservoir containers 42 and 44 are connected through conduits 46 and 48 respectively to venting valve 50. Coupler 52, which has an automatic shut-off valve, is connected to an air supply of pressurized air, which preferably is regulated to have an air pressure of at least 35 psi, for example about 100 psig. Coupler 52 is connected through conduit 54 to pressure regulator 56. Pressure regulator 56 is connected through conduit 58 through interlock valve 60. Valve 60 has a button 62 which must be pressed to open valve 60. When button 62 is pressed, air is conveyed through valve 60 through conduit 64 to selector valve 50. Coupler 66 which has an automatic shut-off valve is connected to conduit 68. Conduit 68 is connected to conduit 54. Coupler 66 provides a connection to pressurized air to operate other devices.

Power control (or generator) 70 is connected to power source 72 through electrical conductor 74 and to power control 70. Power control (or generator) 70 is connected to handpiece 16 through electrical conductor 76.

Feet 80, 80A, 82 and 82A are connected to bottom wall 80B of reservoir housing 12. Feet 80, 80A, 82 and 82A are supported in grooves 84 and 86 in the upper face of scaler housing 14. Feet 80 and 82 are connected to the bottom of the reservoir housing 12.

Reservoir housing 12 has a cover 102 which is opened by pivoting around hinge 104 and 104A. Knob 106 is connected by selector valve stem 106A to valve 50. Turning knob 106 to one side positions the valve 50 to convey fluid from one reservoir through conduit 18. Turn the knob 106 in the other direction from center positions valve 50 to convey fluid from the other reservoir through conduit 18 by pressurization of the respective reservoir chamber. Turning knob 106 to center position vents air from air pilot valve, causing air pilot valve to open and thereby causing external water through conduit 18.

Feet 80 and 80A are supported on groove 160 of scaler housing 14. Feet 82 and 82A are supported in groove 164 in the upper surface of scaler housing 14. Grooves 160 and 164 prevent feet 80, 80A, 82 and 82A from slipping in forward or reversed directions which are perpendicular to the central axis of the groove. Groove 162 is also provided in the upper surface of scaler housing 14. Grooves 160, 162 and 164 are also adapted for placement of handpiece 16 when reservoir housing 12 is not stacked upon scaler housing 14. Holder 170 is adapted to hold handpiece 16. Holder 170 is connected to scaler housing 14. Knob 158 is connected by valve stem 158A to fluid flow control valve 158B. Knob 156 is connected by electrical conductor 156A to power control 70.

Figure 1B:
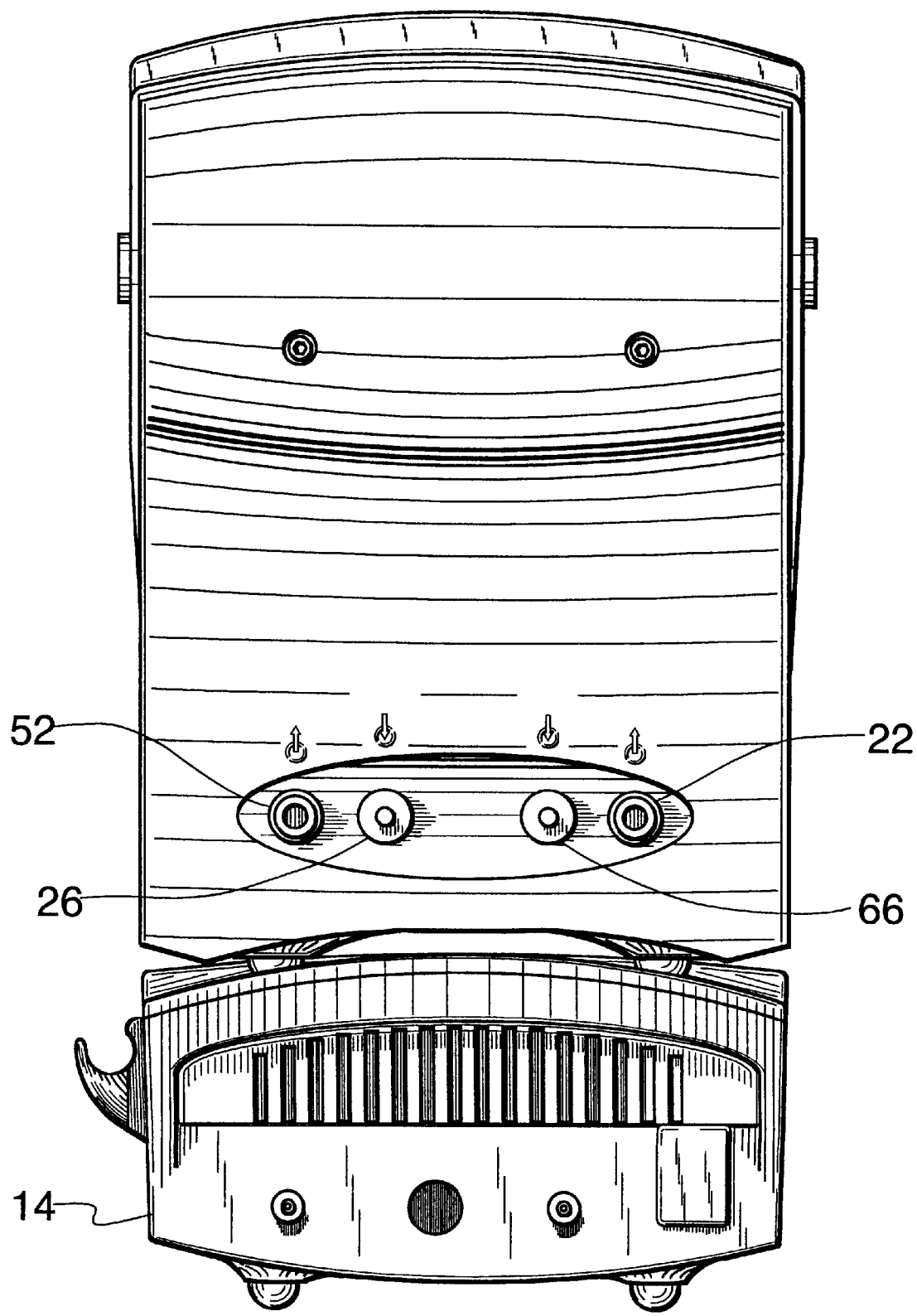
FIG. 1B is a rear view of the stackable reservoir housing stacked upon a scaler housing shown in FIGS. 1 and 1A.
Figure 1C:
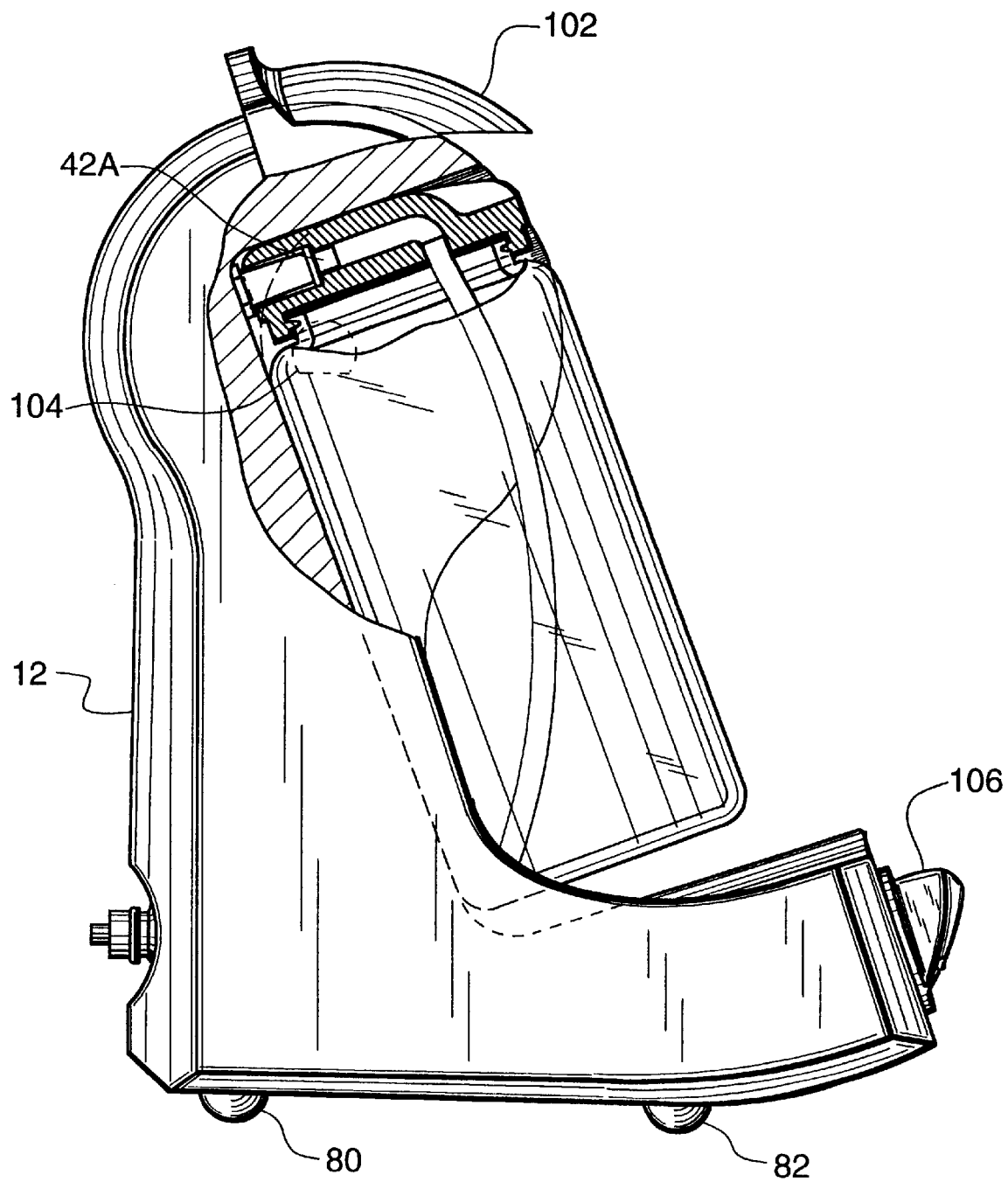
FIG. 1C is a side view of the stackable reservoir housing in accordance with the invention shown in FIGS. 1–9 with the lid partially cut away.
Figure 4:
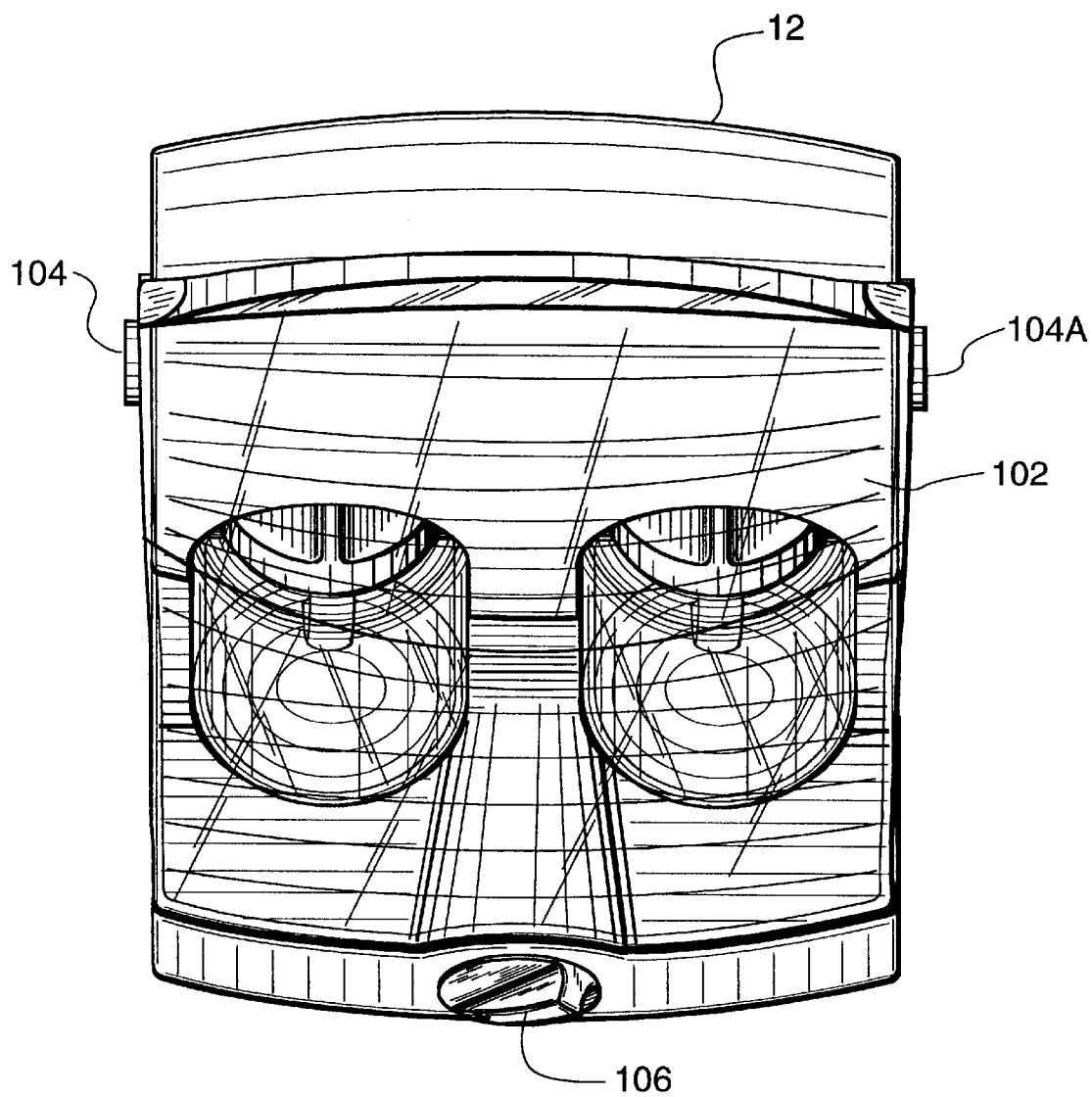
FIG. 4 is a top view of the stackable reservoir housing shown in FIGS. 1–9.
Figure 5:
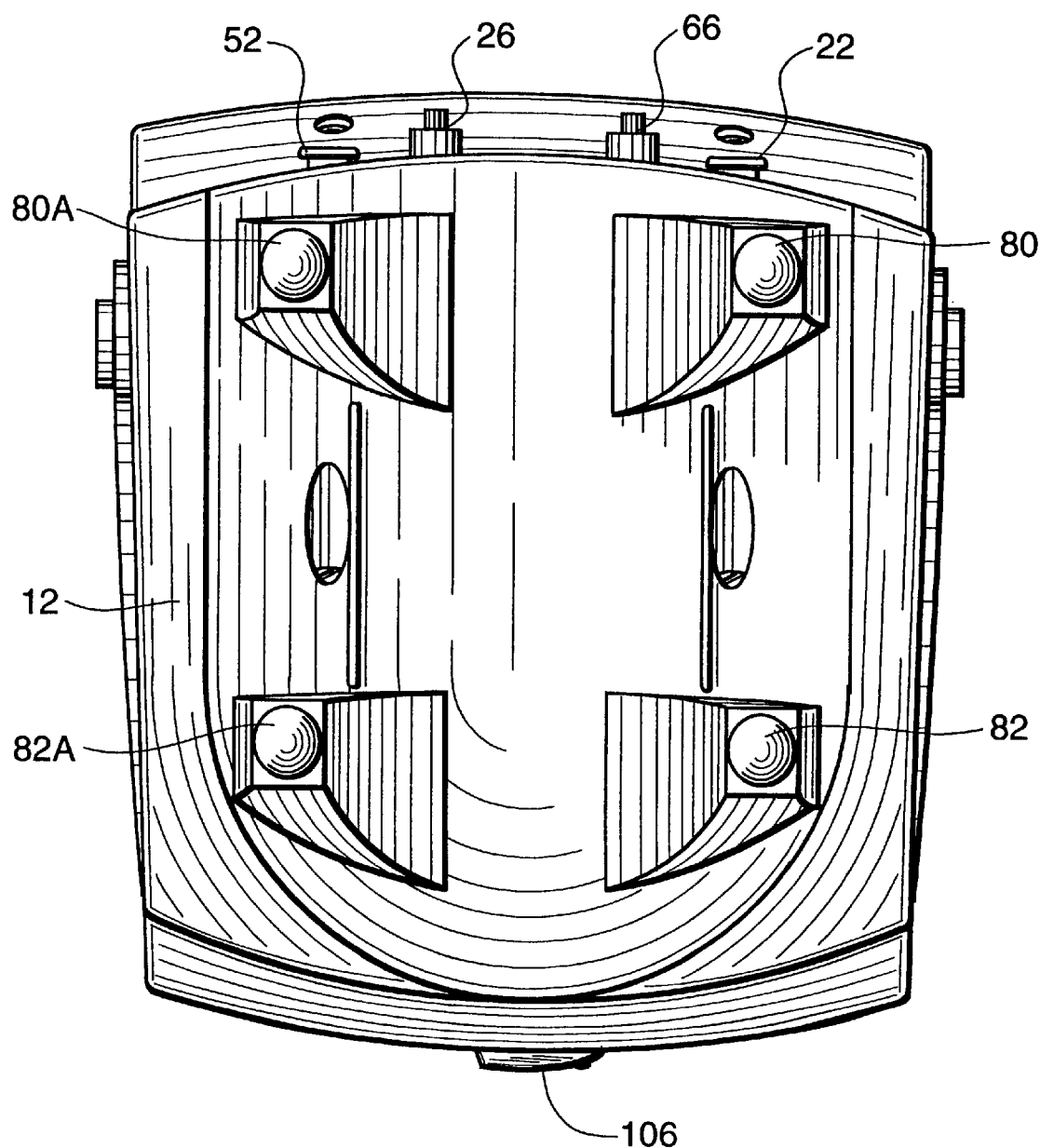
FIG. 5 is a bottom view of a stackable reservoir housing shown in FIGS. 1–9.
Figure 6:
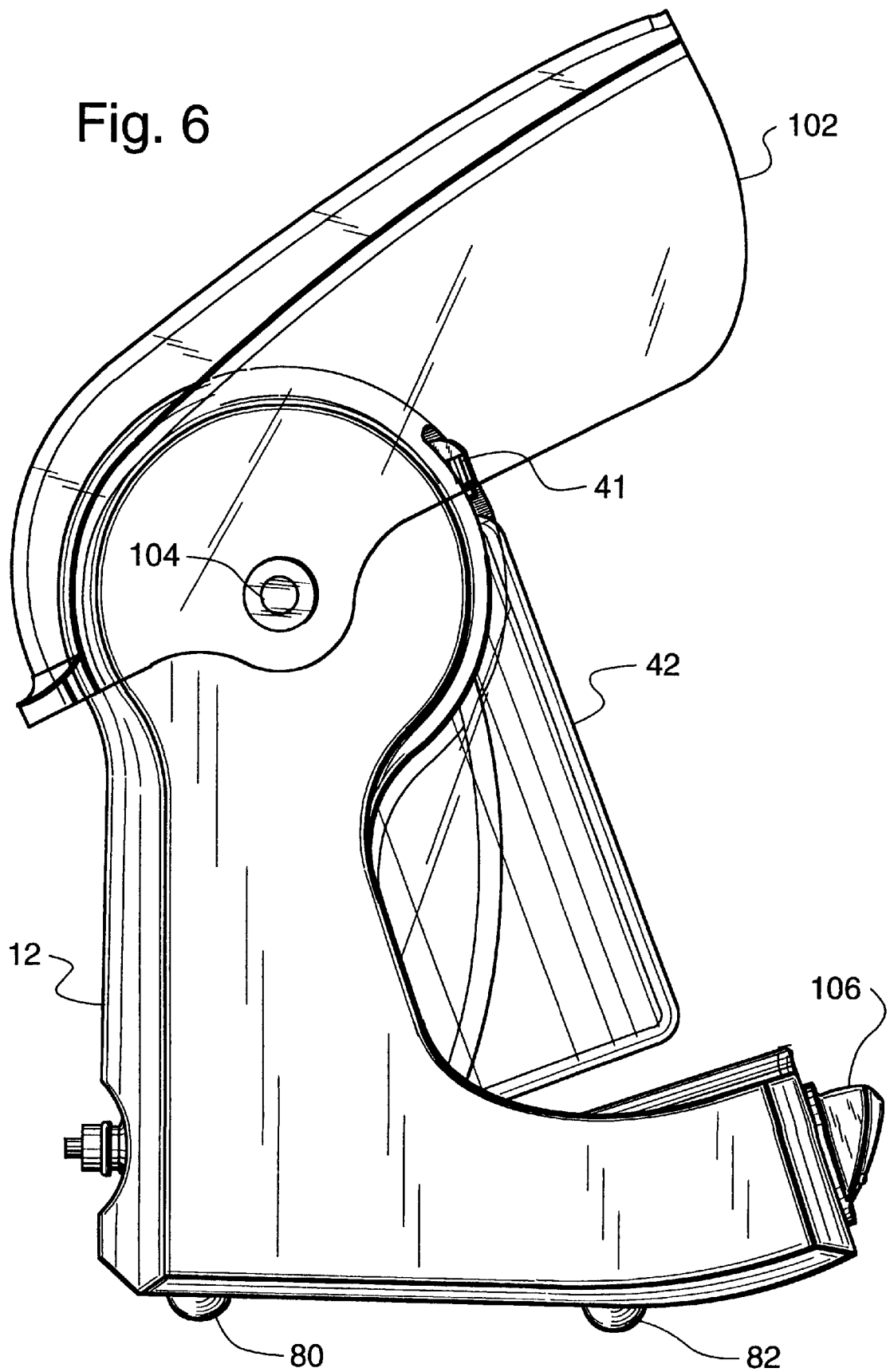
FIG. 6 is a side view of a stackable reservoir housing shown in FIGS. 1–9 with its lid in open position.
Figure 7:
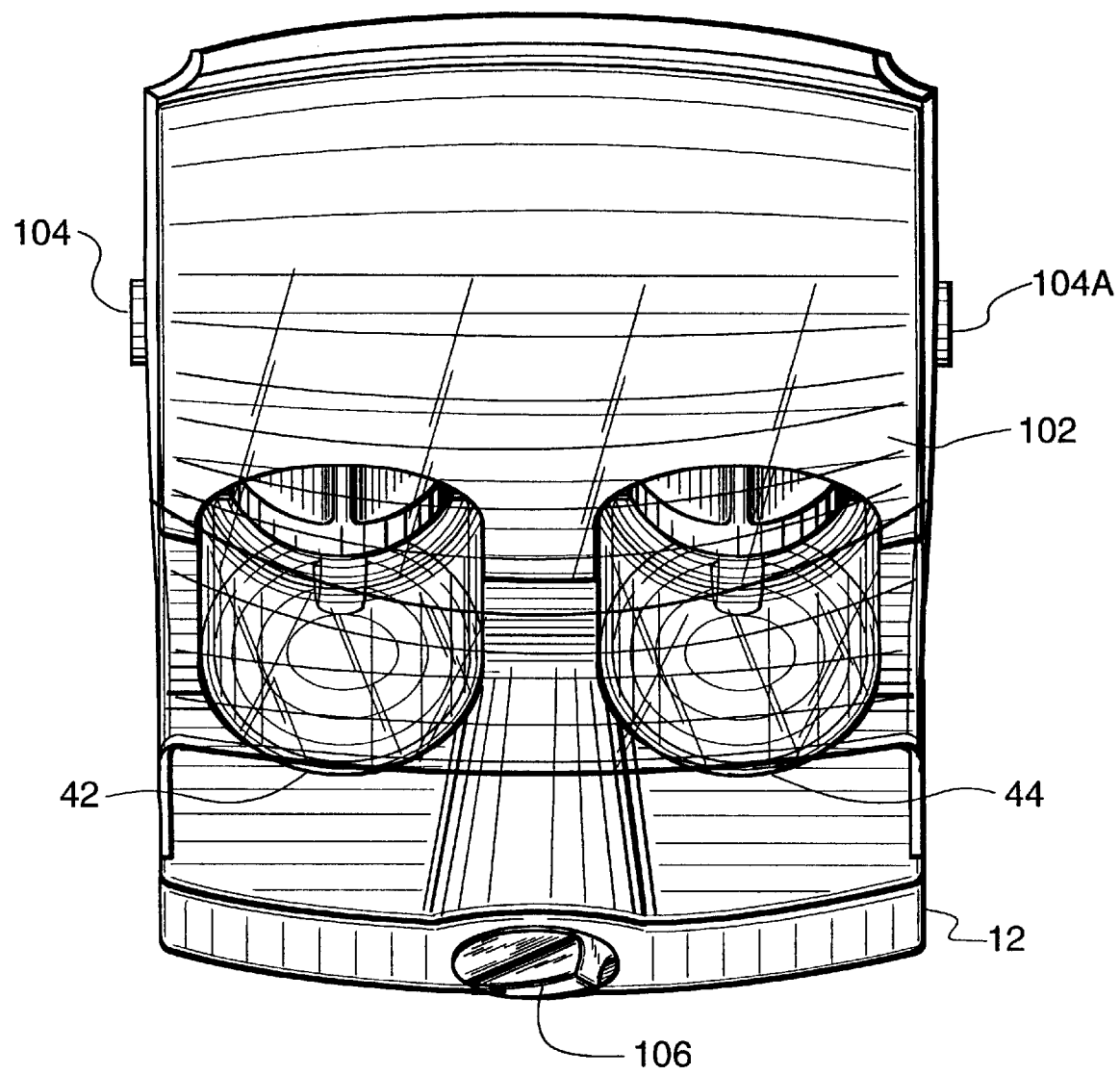
FIG. 7 is a top view of a stackable reservoir housing shown in FIGS. 1–9 with its lid in open position.
Figure 7A:
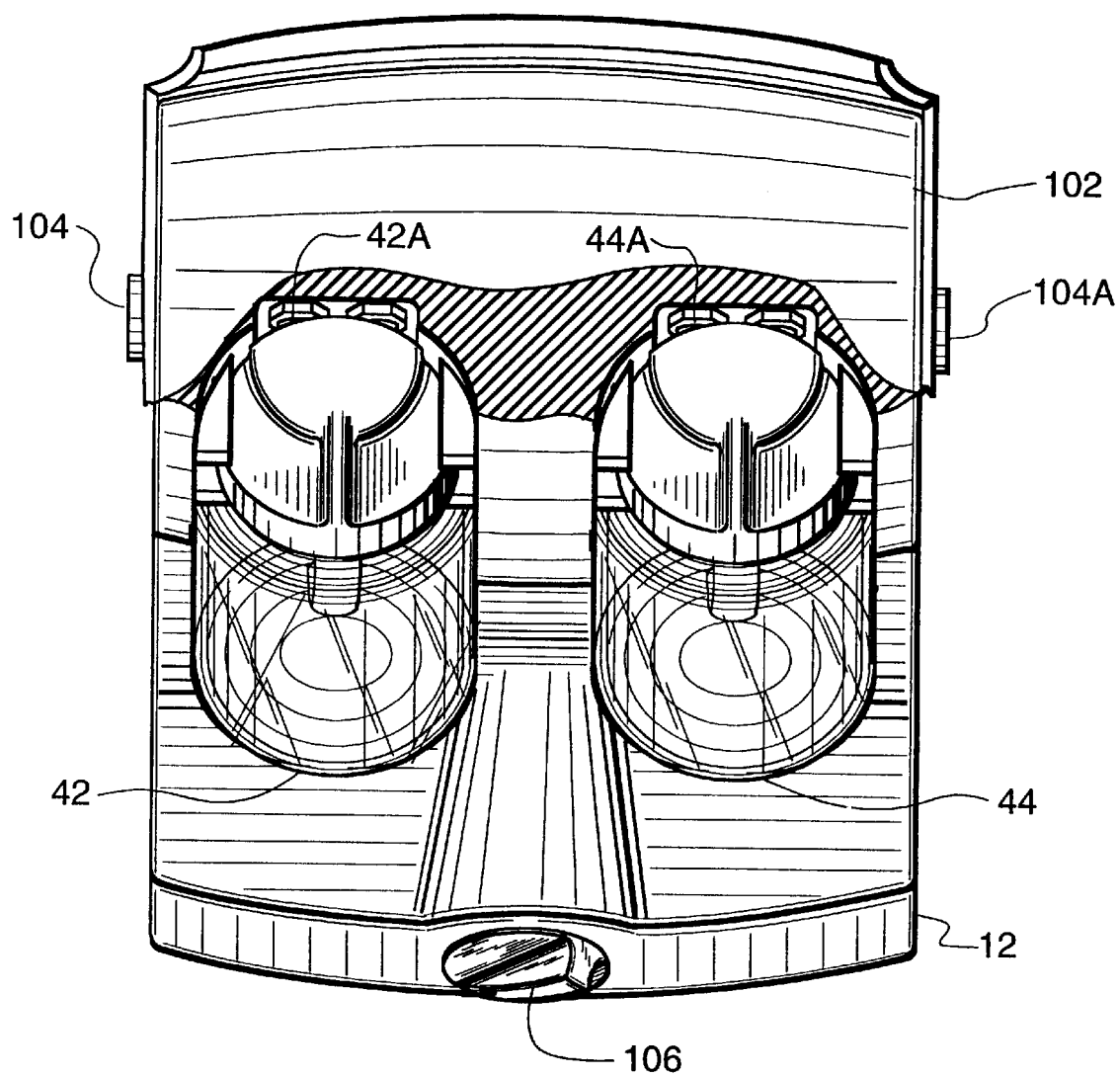
FIG. 7A is a top view of a stackable reservoir housing shown in FIGS. 1–9 with its lid in open position with the lid partially cut away.
Figure 8:
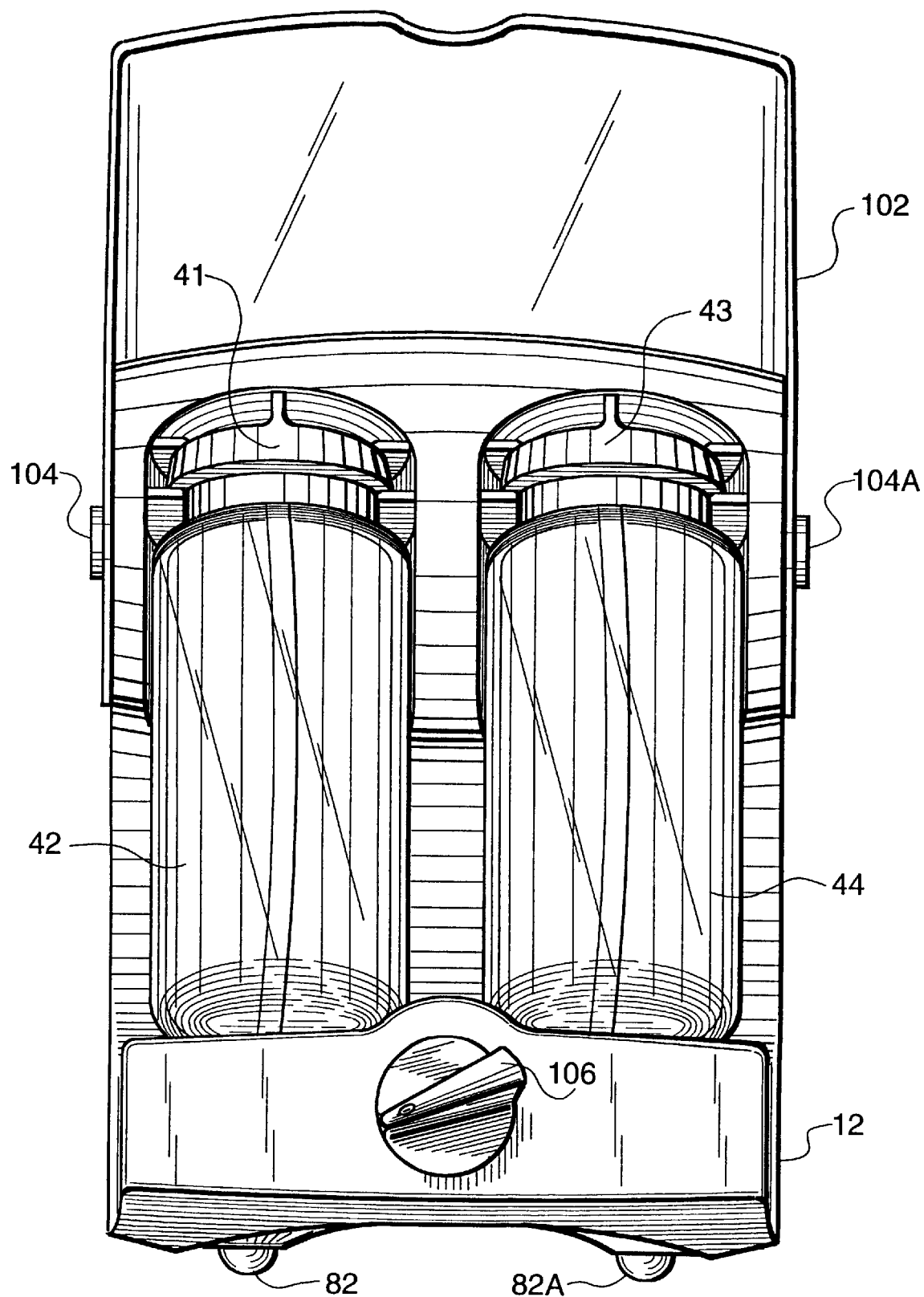
FIG. 8 is a front view of a stackable reservoir housing shown in FIGS. 1–9 with its lid in open position.
Figure 9:
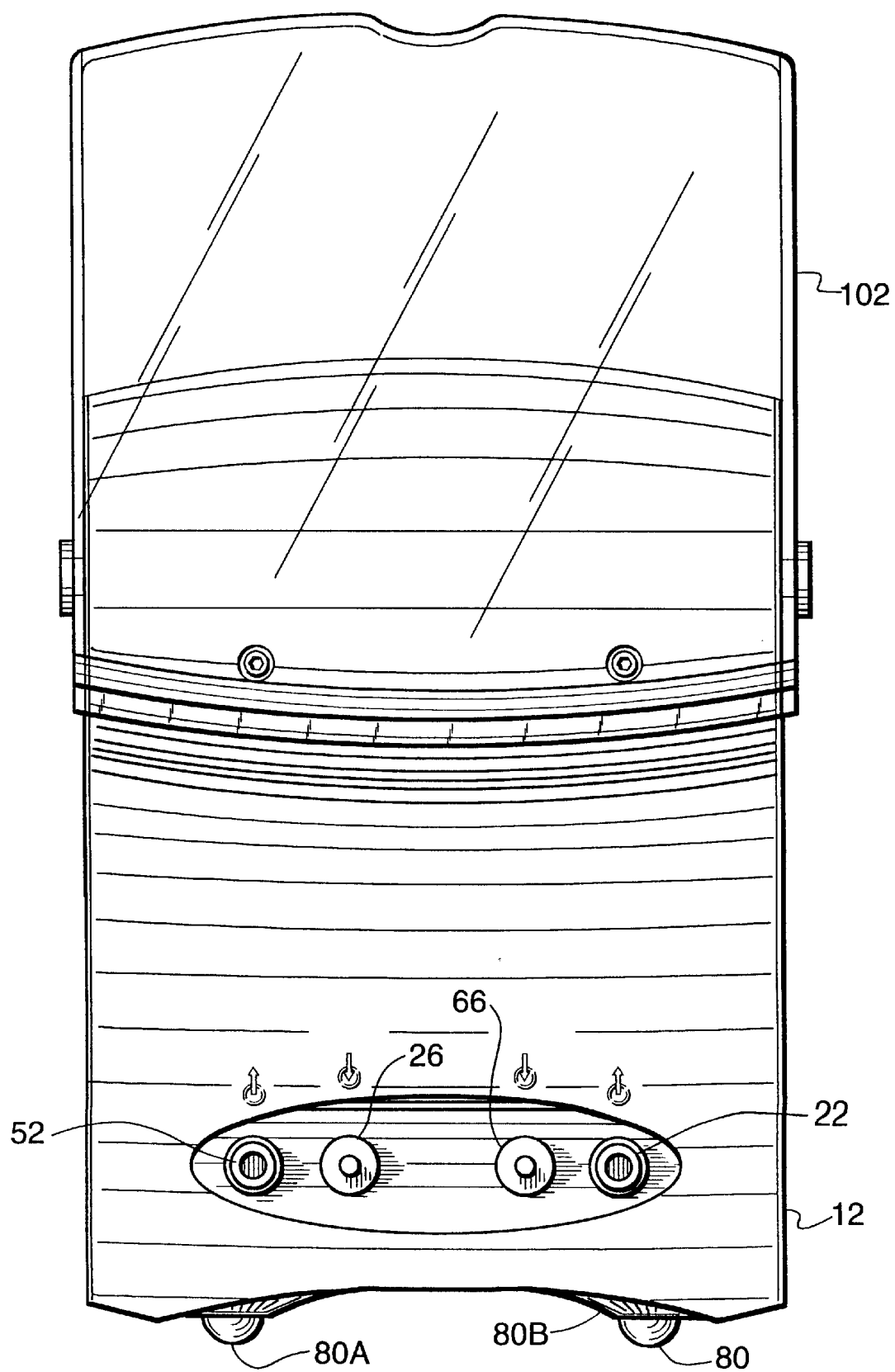
FIG. 9 is a rear view of the stackable reservoir housing shown in FIGS. 1–9 with its lid in open position.
Figure 10:
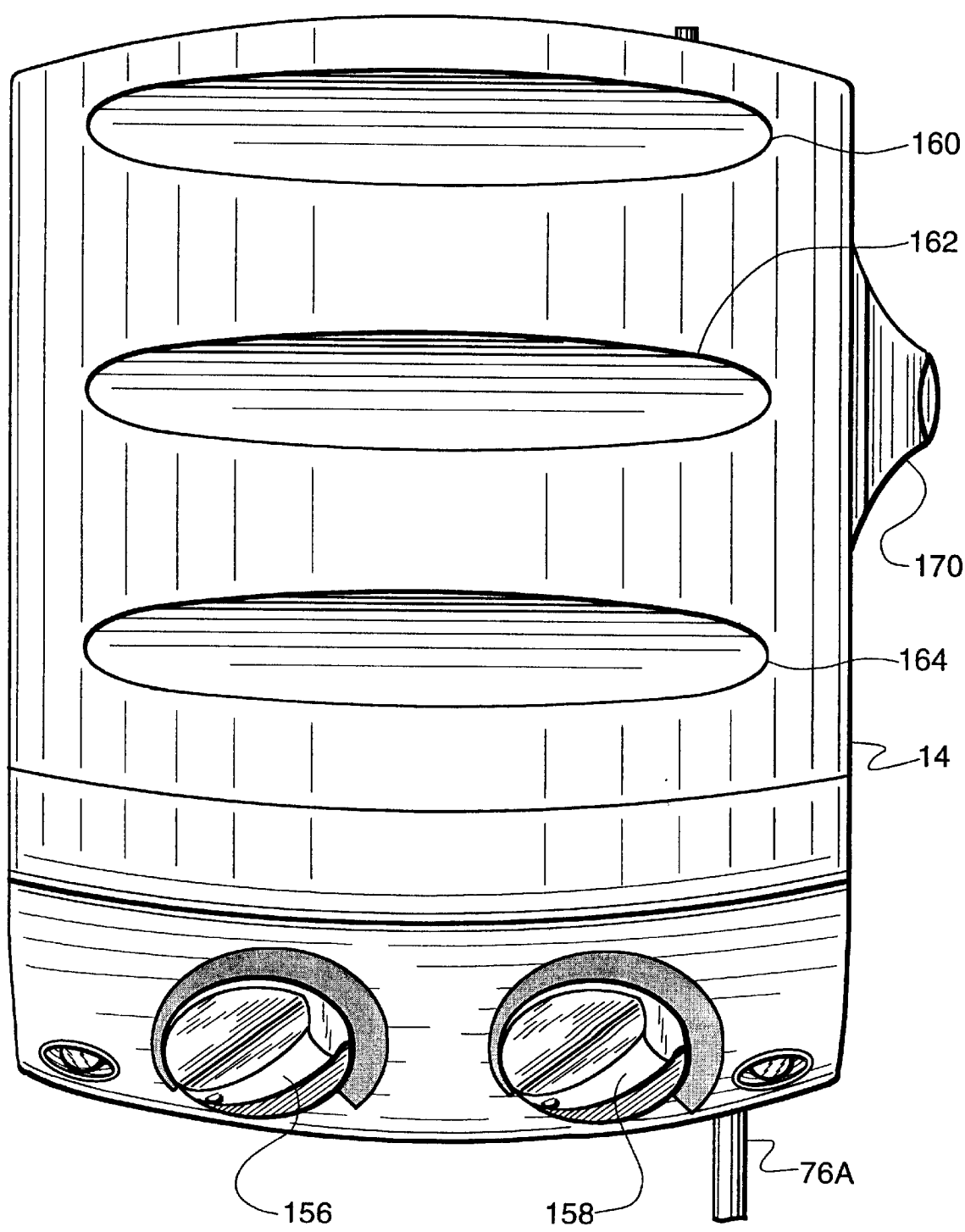
FIG. 10 is a top view of the scaler housing in accordance with the invention shown in FIGS. 10–13.
Figure 11:
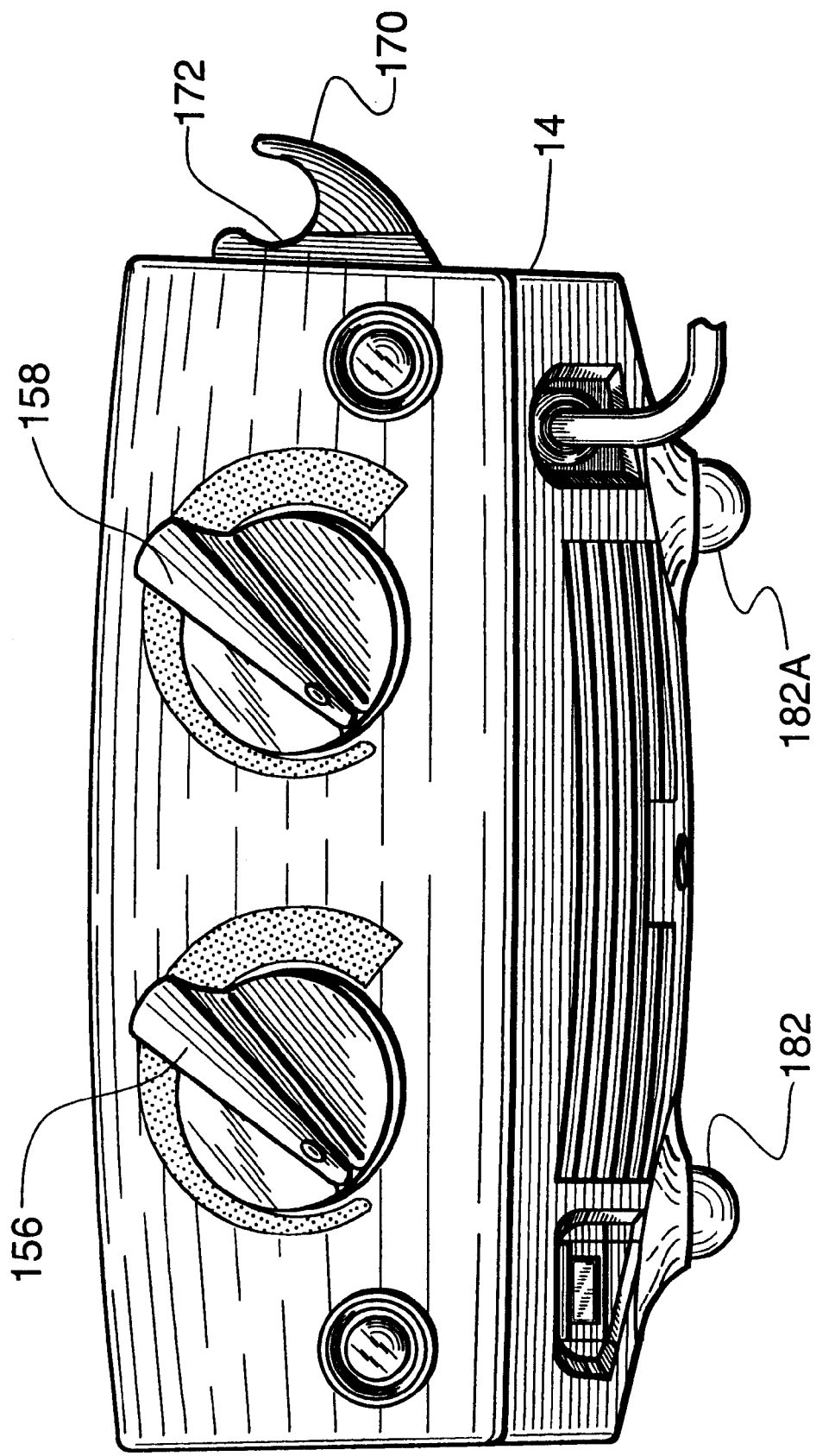
FIG. 11 is a front view of the scaler housing shown in FIGS. 10–13.
Figure 12:
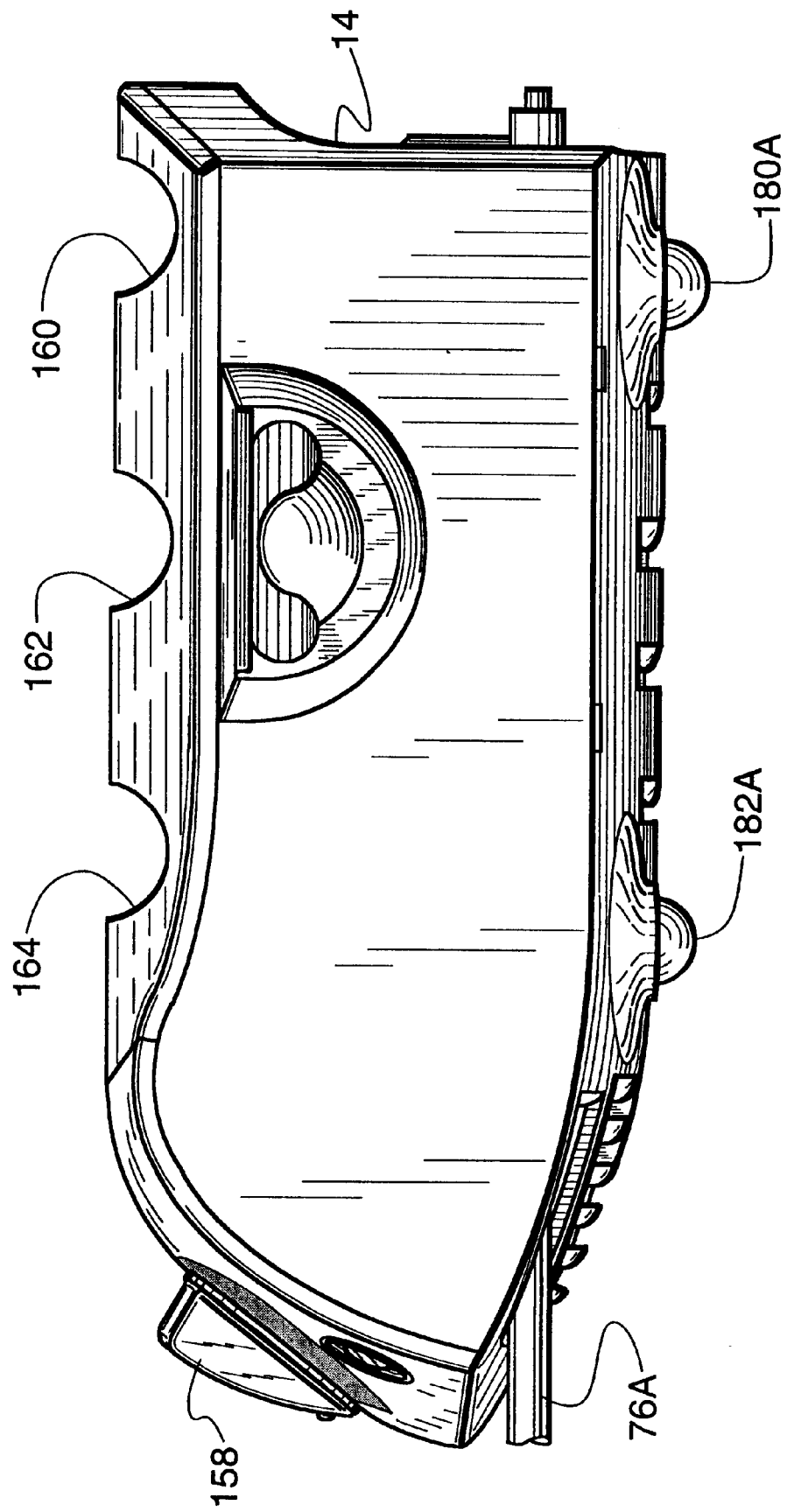
FIG. 12 is a side view of the scaler housing shown in FIGS. 10–13.
Figure 13:
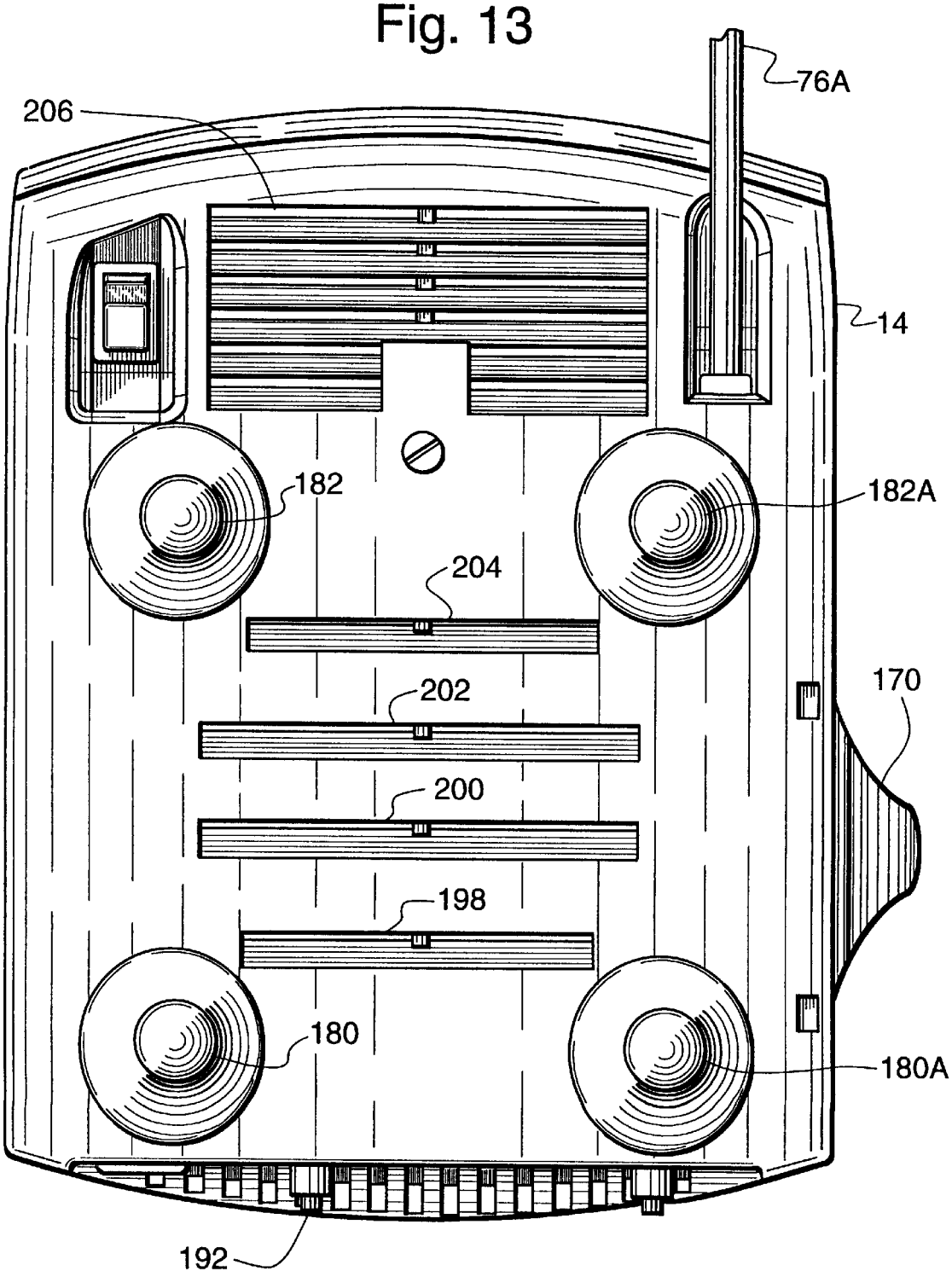
FIG. 13 is a bottom view of the scaler housing shown in FIGS. 10–13.

When lid 102 is in closed position, caps 41 and 43 are held by lid 102 onto the adjacent fluid connectors 42A and 44A as shown in FIGS. 1A and 7A.

Scaler housing 14 is supported by feet 180, 180A, 182 and 182A.

Vents 198, 200, 202, 204 and 206 in the lower wall of scaler housing 14 allow cooling by convection.

Fluid conduit 24 and electrical conductor 76 are enclosed by flexible plastic conduit 76A.

Conduit 20 connected to connector 22 at one end and at the other end to connector 192.

Foot switch 170A is connected by electrical current conductor 170B to power control 70.

Figure 14A:
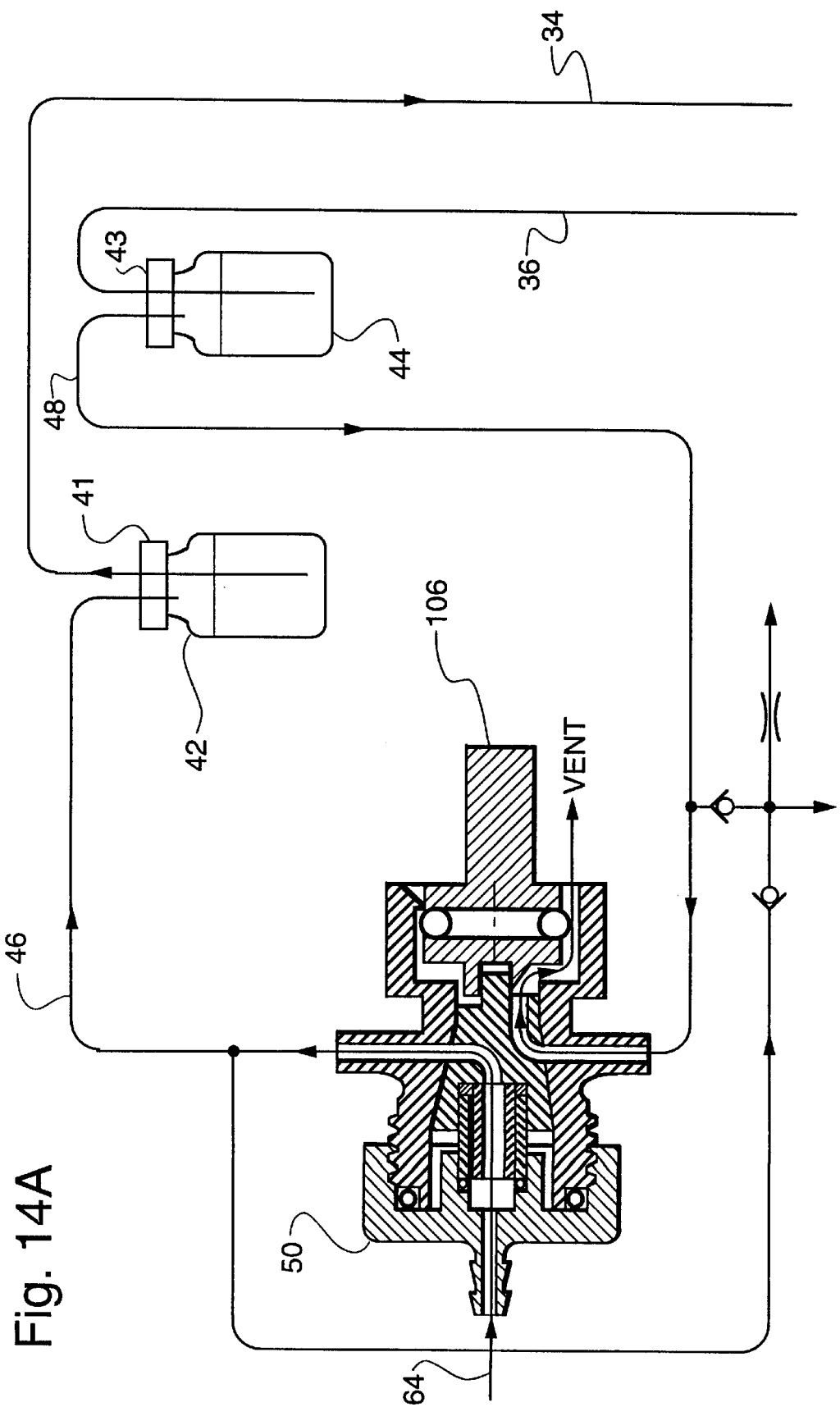
FIGS. 14A, 14B and 14C are schematic diagrams of the air pressure/venting distribution valve (selector valve) in three different positions.
Figure 14B:
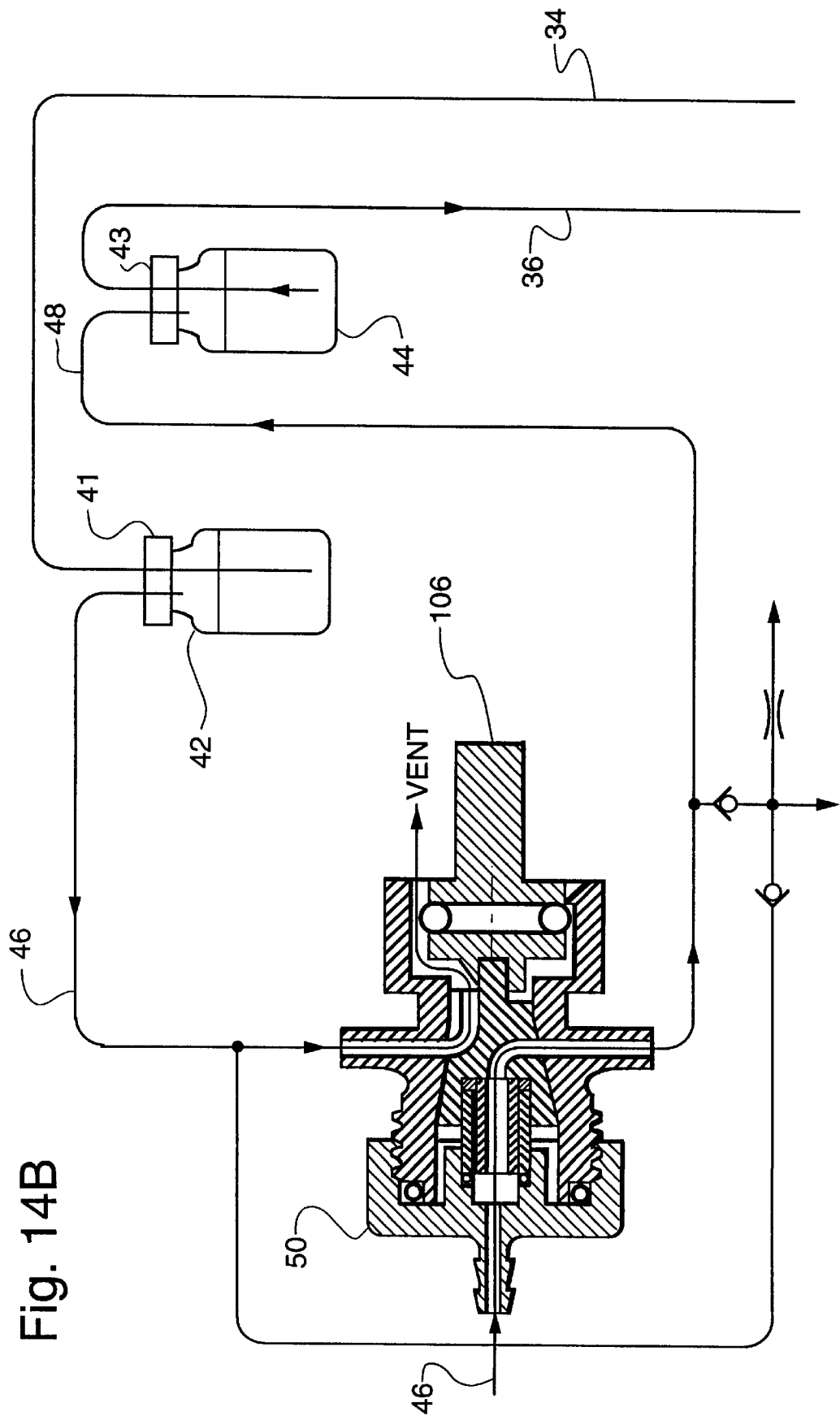
Figure 14C:
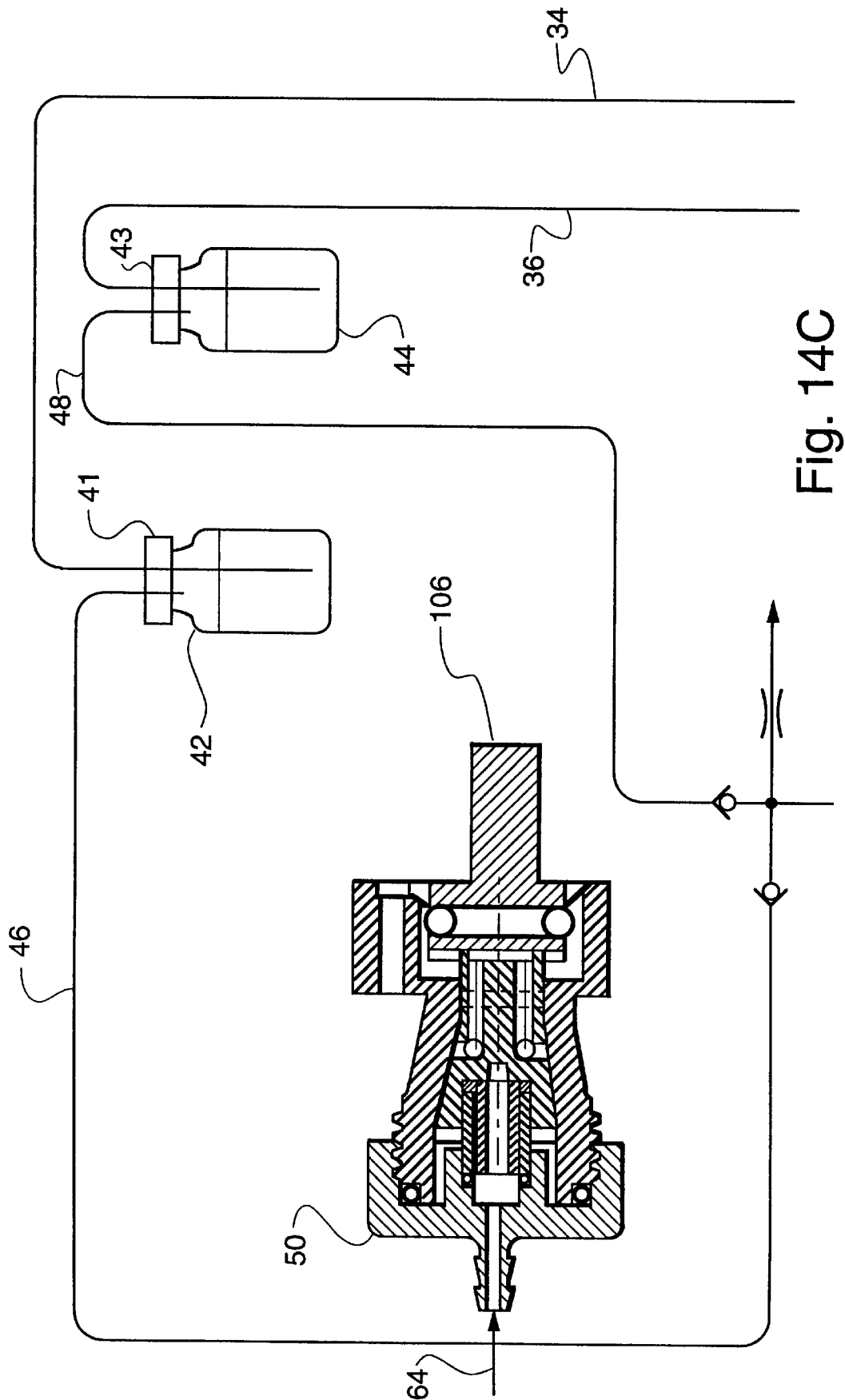
Figure 15:
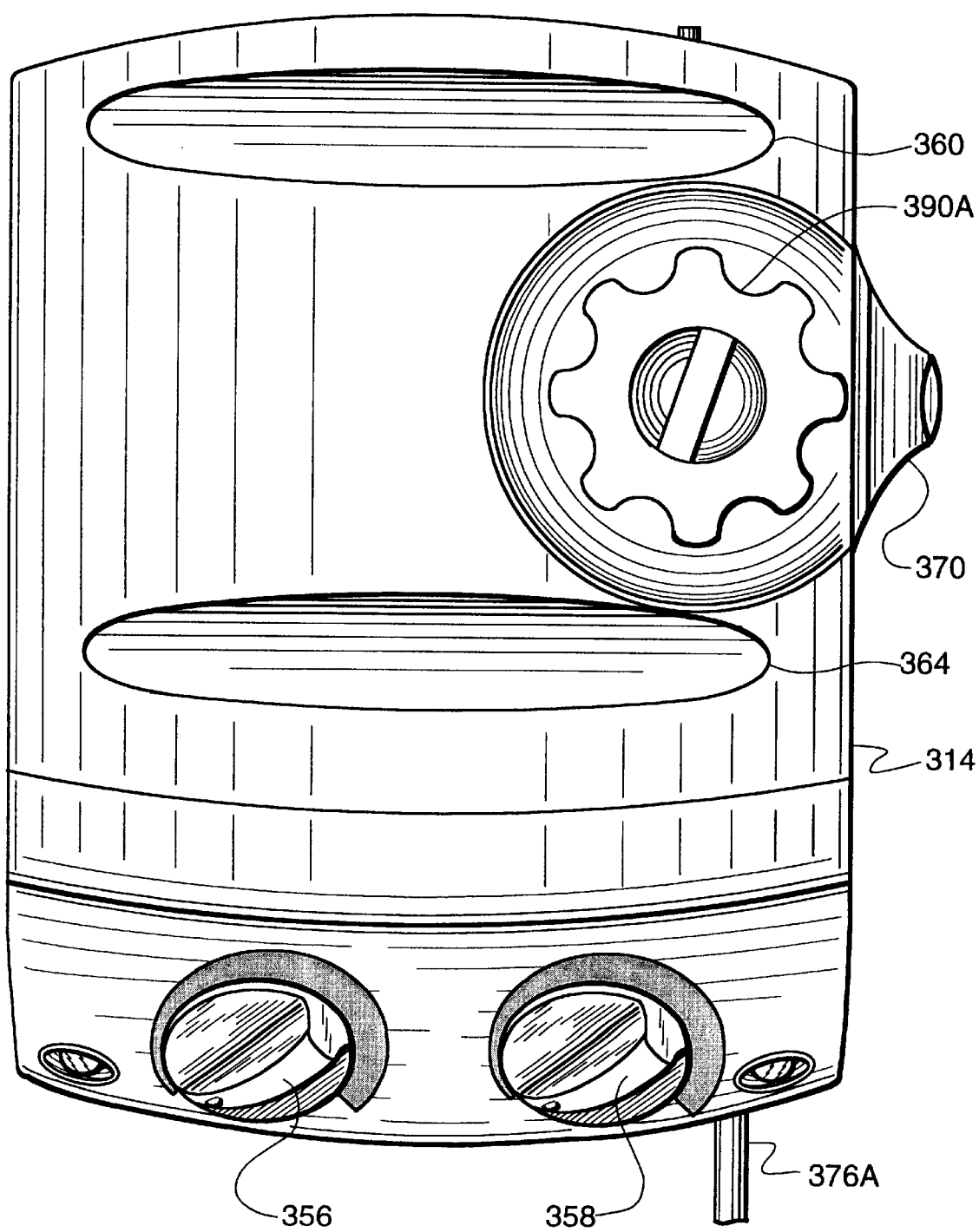
FIG. 15 is a top view of a air polishing housing shown in FIGS. 15–18.
Figure 16:
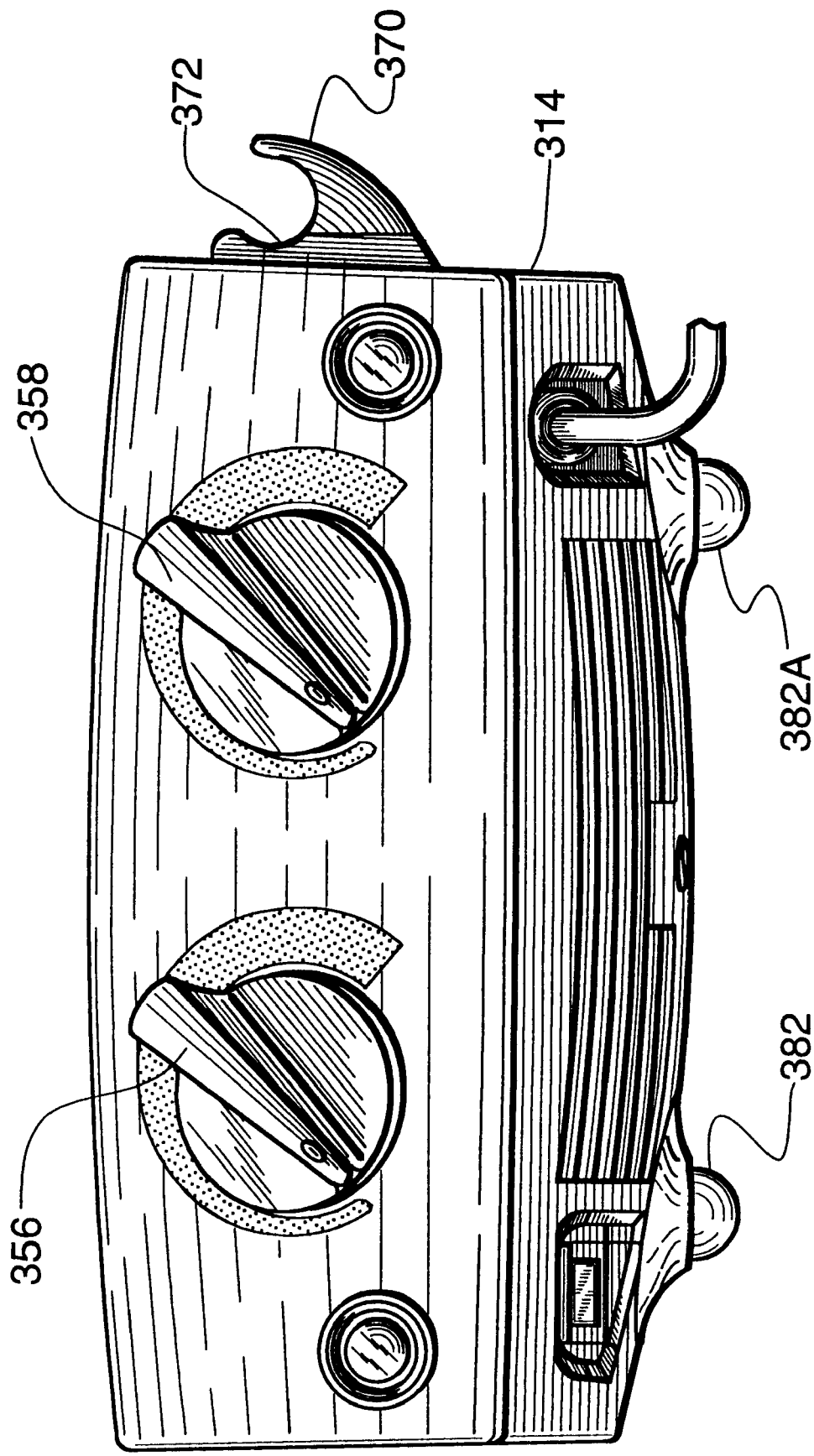
FIG. 16 is a front view of the air polishing housing shown in FIGS. 15–18.
Figure 17:
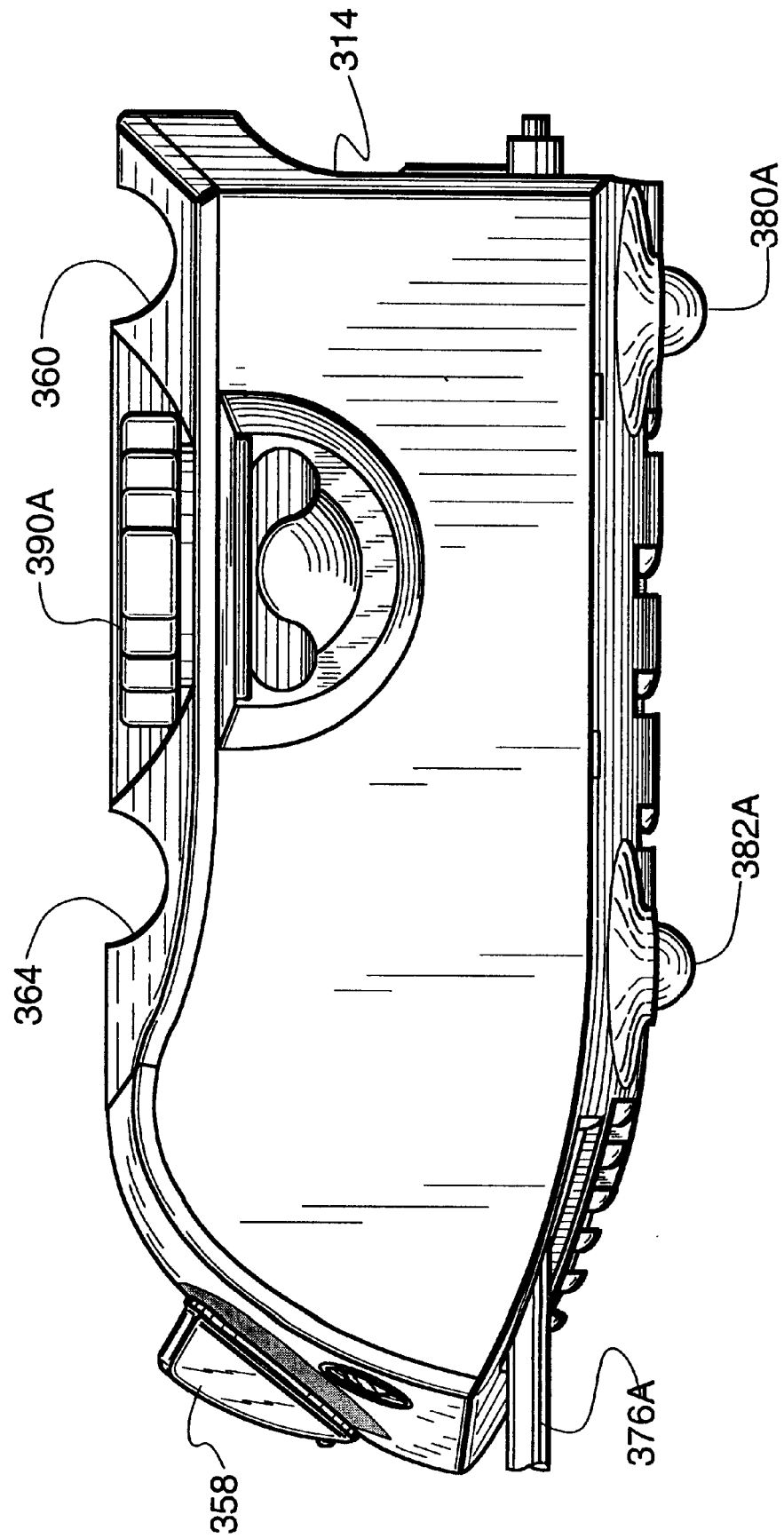
FIG. 17 is a side view of the air polishing housing shown in FIGS. 15–18.
Figure 18:
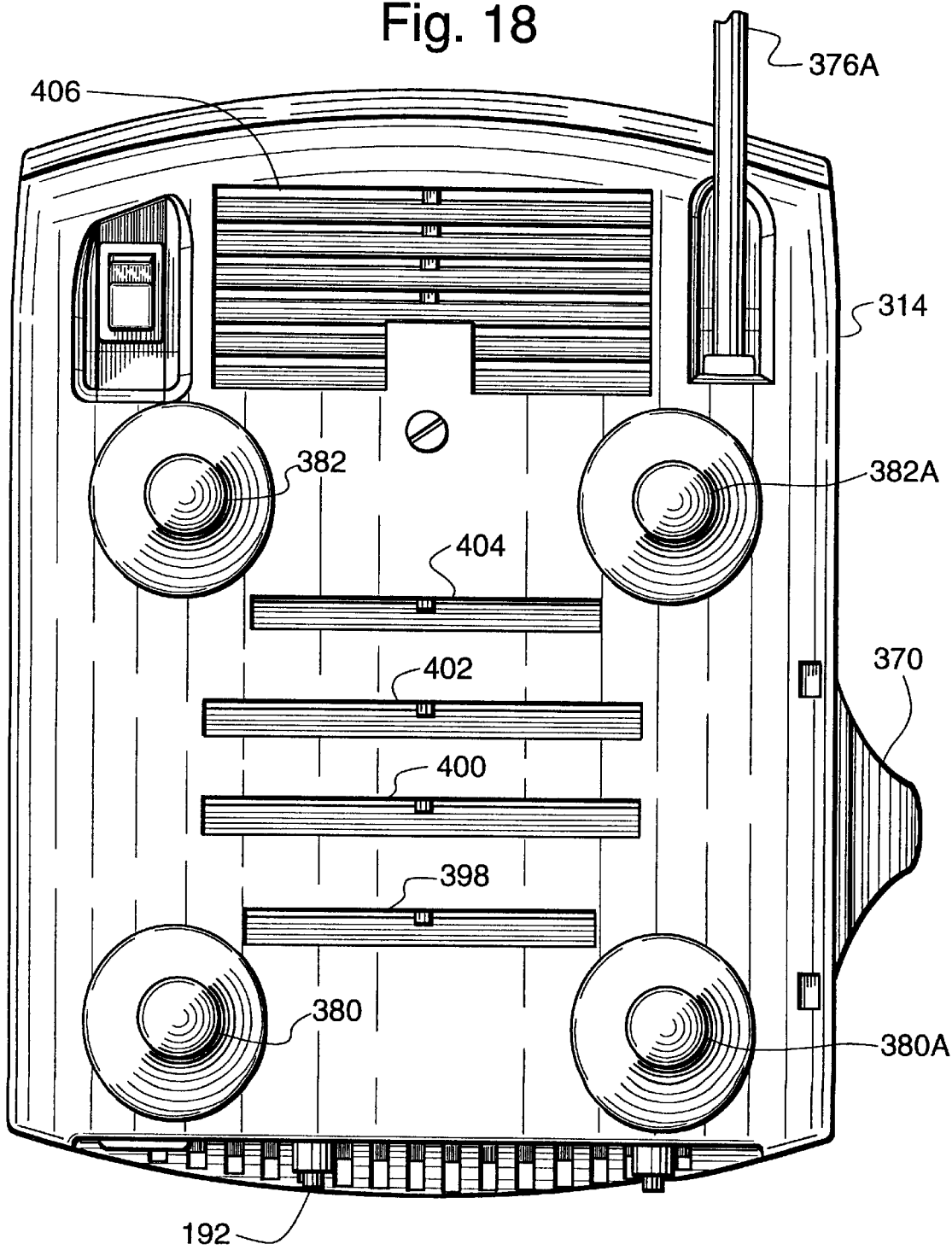
FIG. 18 is a bottom view of the air polishing housing shown in FIGS. 15–18.
Figure 19:
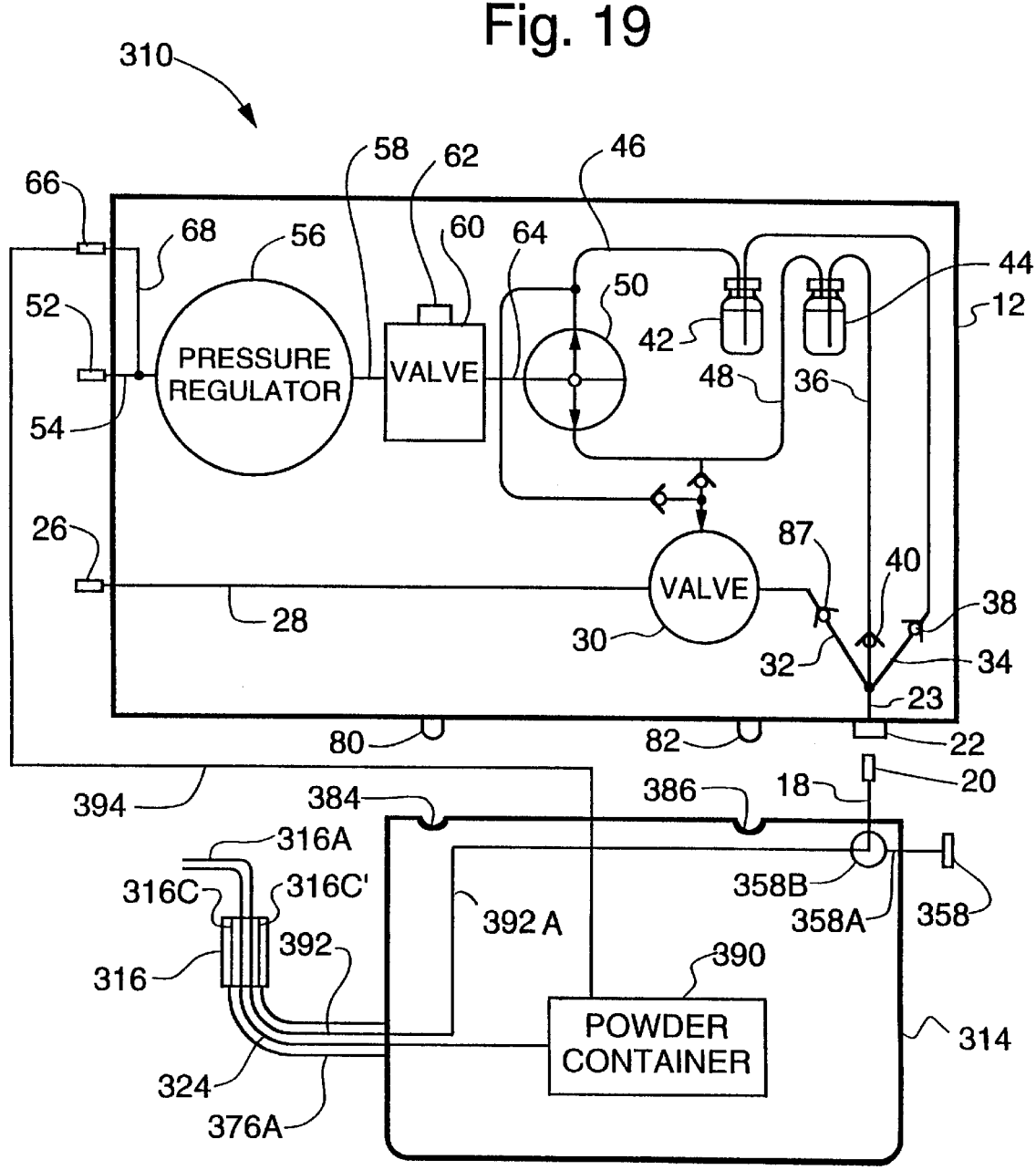
FIG. 19 is a schematic diagram of the stacking dental reservoir shown in FIGS. 1C and 2–9 in use with the air polishing system shown in FIGS. 15–18.
Figure 20:
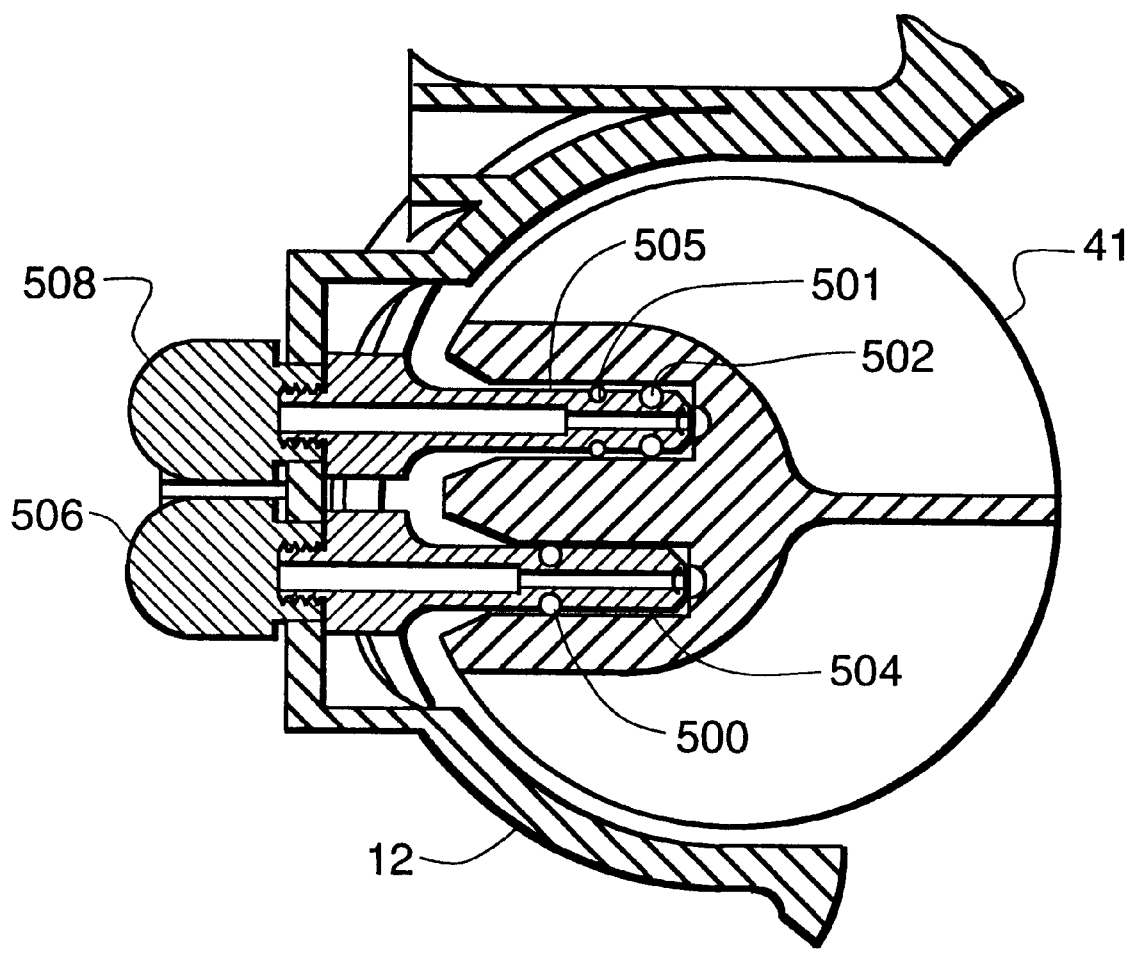
FIG. 20 is a schematic diagram of a partial cross-sectional top view of a reservoir housing showing a cap for a container.

As shown in FIGS. 14, 14A, 14B and 14C valve 50 is rotated to three different positions by turning knob 106. As shown in FIG. 14A by turning valve 50 to the position shown air entering valve 50 through line 64 leaves valve 50 through line 56 to pressurize container 42 causing fluid to flow from container 42 through line 34. As shown in FIG. 14B by positioning valve 50 in the position shown, air enters valve 50 through line 46 and leave valve 50 through line 48. Air in line 48 pressurizes container 44 causing fluid from container 44 to flow through line 36. As shown in FIG. 14C by positioning valve 50 as shown, neither container 42 nor container 44 is pressurized, and fluid does not flow from either container in this position of valve 50. Rather in the position of valve 50 shown in FIG. 14C, air pressure is not supplied to valve 30 and existing air pressure is reduced by a bleed port, opening air pilot valve 30 allowing fluid to flow through line 28 to line 32, as shown in FIG. 14.

With more particular reference to FIGS. 15–19, it is seen that air polishing base housing 314 is connected to polishing handpiece 316 having coils 316C and 316C'. Air polishing base housing 314 has grooves 360 and 364 in the upper face thereof. Feet 80 and 82 of reservoir housing are positioned in grooves 360 and 364 of the upper face of the air polishing base housing when the reservoir housing is in stacked position on the air polishing base housing. Outer container 390 has container cap 390A. Powder container 390 is connected through a conduit 394 to coupler 66 to provide air pressure in powder container 390. Powder from powder container 390 is conveyed under pressure through conduit 392 to handpiece 316. Fluid is conveyed through line 18 to air polishing base housing 314. Fluid is conveyed from air polishing 314 through conduit 324 to handpiece 316. Handpiece 316 is provided with a mixing tip 316A which sprays liquid from an outer concentric orifice and sprays powder from an inner-circular orifice. Thus, it provides an annulus of liquid around a circular stream of powder which mixes in the spray prior to polishing the tooth surface. Conduits 392 and 324 are enclosed by flexible plastic cover 376A. Air polishing base housing 314 is supported by feet 380, 382, 380A and 382A. The lower face of air polishing base housing 314 has vent 398, 400, 402, 404 and 406. Handpiece 316 is adapted to be held by holder 370. Knobs 356 and 358 are connected to a variable power control unit, and a fluid flow control valve respectively. Knob 358 is connected by valve stem 358A to fluid flow control valve 358B.

Upon disengaging reservoir cap 41 from housing 12, O-ring 500 unseals relieving any residual air pressure in container 42, with further outward movement of the cap, O-ring 501 is unseated, and a vent hole is exposed to atmospheric pressure, thereby allowing any fluid remaining in the passageway of the coupler to move back into container 42 avoiding spillage during final withdrawal of cap 41 and container 42 from housing 12 past O-ring 501. Connectors (or couplings) 504 and 505 are connected in fluid flow communication with connectors (or couplings) 506 and 508 respectively. Connector 506 is connected in fluid flow communication with conduit 46. Connector 508 is connected in fluid flow communication with conduit 34.

It will be apparent to those skilled in the art that various modifications and changes may be made in the practice and use of the present invention without departing from the scope thereof as set forth in the following claims.

What is claimed is:

1. A stacking system comprising:
   a reservoir housing,
   a cover consisting essentially of clear transparent plastic,
   a base housing and
   a handpiece
   said reservoir housing supporting a readily removable container said reservoir housing having feet, said cover being pivotally connected to said reservoir housing,
   said reservoir housing supporting a first and a second housing fluid flow connector, said container having a cap with a first and a second cap fluid flow connector, said first housing connector being connected to said first cap connector, said second housing connector being connected to said second cap connector, said handpiece being connected to said base housing, said base housing being connected to a base connecting conduit, said base connecting conduit being connected to said reservoir housing,
   said reservoir housing having a base end and a hinge end, said base end being connected to said feet said hinge end being substantially opposite to said base end, said hinge end supporting a hinge, said hinge end being connected to said first and second housing fluid flow connector,
   said cover being connected to said hinge and said cover being pivotable between an open position and a closed position, said cover in closed position preventing said cap from moving sufficiently for said first cap connector to disengage from said first housing connector,
   said reservoir housing being supported by and positioned above said base housing, said base housing having an upper face, said upper face having grooves, said feet being positioned in said grooves, said container being in fluid flow communication with said handpiece.

2. The system of claim 1 wherein said container is connected through conduit means to a valve.

3. The system of claim 2 wherein said valve is connected through a conduit to a source of air at a pressure of at least 35 psi.

4. The system of claim 2 wherein said reservoir housing supports a second readily removable container, said second container being connected through a conduit to said valve.

5. The system of claim 1 wherein said base housing encloses a base housing conduit.

6. The system of claim 5 wherein said base housing conduit is connected to a base housing connector, said base housing connector being connected to said base connecting conduit.

7. The system of claim 1 wherein said container encloses a fluid, said fluid comprising medicament.

8. The system of claim 7 wherein said container is enclosed by said reservoir housing when said cover is in closed position.

9. A stacking system comprising a fluid reservoir housing, a base housing, and an ultrasonic dental handpiece having an electrically conducting coil,
   said reservoir housing having feet, said feet being supported by said base housing,
   said reservoir housing enclosing a first container and a second container,
   said first and second containers being connected in flow fluid communication to a valve, said valve being connected in fluid flow communication with said handpiece, said base housing enclosing a power control circuit, said power control circuit being connected to said coil in said handpiece, said reservoir housing having a cover consisting essentially of clear transparent plastic, said first container having a first container fluid flow connector, said reservoir housing having a first reservoir fluid flow connector, said first reservoir housing connector engaging said first container connector, said reservoir housing having a base end and a hinge end, said base end being connected to said feet, said hinge end being substantially opposite to said base end, said hinge end supporting a hinge, said hinge end being connected to said first and second housing fluid flow connector, said cover being connected to said hinge, said cover being positioned against said first container to prevent movement of said first container whereby said first container connector is held in said first reservoir connector, while said cover is in closed position.

10. A stacking system comprising a fluid reservoir housing (12), a base housing, and a dental handpiece having a mixing tip, said reservoir housing having a cover consisting essentially of clear plastic, said reservoir housing being supported by an upper face of said base housing, said reservoir housing supporting a readily removable container said reservoir housing having feet, said cover being pivotally connected to said reservoir housing by a hinge, said reservoir housing supporting a first and a second housing fluid flow connector, said container having a cap with a first and a second cap fluid flow connector, said first housing connector being connected to said first cap connector, said second housing connector being connected to said second cap connector, said handpiece being connected to said base housing, said reservoir housing having a base end and a hinge end, said base end being connected to said feet said hinge end being substantially opposite to said base end, said hinge end supporting said hinge, said hinge end being connected to said first and second housing fluid flow connector, said container being connected through conduit means to a valve, said conduit means being connected in fluid flow communication with said tip.

11. A stacking system comprising:

a reservoir housing, and a cover consisting essentially of clear transparent plastic, said reservoir housing supporting a readily removable container said reservoir housing having feet, said cover being pivotally connected to said reservoir housing, said reservoir housing supporting a first and a second housing fluid flow connector, said container having a cap with a first and a second cap fluid flow connector, said first housing connector being connected to said first cap connector, said second housing connector being connected to said second cap connector, said handpiece being connected to said base housing, said reservoir housing having a base end and a hinge end, said base end being connected to said feet said hinge end being substantially opposite to said base end, said hinge end supporting a hinge, said hinge end being connected to said first and second housing fluid flow connector, said reservoir housing having first, second and third sides, said cover being connected to said hinge, said cover being pivotable between an open position and a closed position, said cover in closed position preventing said cap from moving sufficiently for said cap connector to disengage from said housing connector, in said closed position said cover extending over a substantial portion of said hinge end and said first and second sides, and a major portion of said third side, in said open position said cover extending over at least a major portion of said hinge end, and a substantial portion of said first and second sides, said third side being open allowing access to said container.

* * * * *